United States Patent
Sung et al.

(10) Patent No.: US 7,183,077 B2
(45) Date of Patent: Feb. 27, 2007

(54) PROMOTERS AND GENE EXPRESSION METHOD BY USING THE PROMOTERS

(75) Inventors: Moon-Hee Sung, Taejon (KR); Seung-Goo Lee, Taejon (KR); Seung-Pyo Hong, Taejon (KR); Hwa-Jung Seo, Taegu (KR)

(73) Assignees: BioLeaders Corporation, Taejon (KR); Takara Bio Inc., Otsu (JP)

( * ) Notice: Subject to any disclaimer, the term of this patent is extended or adjusted under 35 U.S.C. 154(b) by 434 days.

(21) Appl. No.: 10/258,482

(22) PCT Filed: Apr. 26, 2001

(86) PCT No.: PCT/JP01/03607

§ 371 (c)(1),
(2), (4) Date: Oct. 25, 2002

(87) PCT Pub. No.: WO01/83787

PCT Pub. Date: Nov. 8, 2001

(65) Prior Publication Data

US 2003/0190706 A1    Oct. 9, 2003

(30) Foreign Application Priority Data

Apr. 27, 2000 (JP) ............................. 2000-128528

(51) Int. Cl.
*C12P 21/00* (2006.01)
*C12N 1/21* (2006.01)
*C12N 15/70* (2006.01)
*C12N 15/74* (2006.01)
*C07H 21/04* (2006.01)

(52) U.S. Cl. ................. 435/69.1; 435/252.31; 435/252.33; 435/320.1; 536/23.1; 536/24.1

(58) Field of Classification Search ............... 536/24.1, 536/23.1; 435/320.1, 252.3, 252.31, 252.33, 435/69.1
See application file for complete search history.

(56) References Cited

U.S. PATENT DOCUMENTS 4,666,836 A * 5/1987 Inouye et al. ............... 435/69.1

FOREIGN PATENT DOCUMENTS

| KR | 98050070 A | 9/1998 |
|----|-----------|--------|
| KR | 98078034 A | 11/1998 |
| KR | 99039948 A | 6/1999 |

OTHER PUBLICATIONS

Ian G. Fotheringham et al.; Journal of Bacteriology, vol. 180, No. 16, Aug. 1998, pp. 4319-4323.
Kor. J. Microbiol. Biotechnol., vol. 27, pp. 184-190 (1999).
Biochimica et Biophysica ACta, vol. 1350, No. 1, pp. 38-40 (1997).

* cited by examiner

*Primary Examiner*—Nancy Vogel
(74) *Attorney, Agent, or Firm*—Birch, Stewart, Kolasch, and Birch, LLP

(57) ABSTRACT

To provide a promoter, a recombinant DNA, a gene expression vector, an expression vector, and a transformant, which are capable of expressing a gene without inducing gene expression with an inducer; and a method for producing a protein and a kit therefor, which can be operated easily and performed inexpensively by convenient and inexpensive steps. An isolated DNA having the nucleotide sequence of SEQ ID NO: 1 or 2 of Sequence Listing or a fragment thereof, wherein the isolated DNA exhibits a constitutive promoter activity in *Escherichia coli* or a bacterium belonging to the genus *Bacillus*; an isolated DNA having a nucleotide sequence of a nucleic acid capable of hybridizing to the above DNA, wherein the isolated DNA exhibits a constitutive promoter activity in *Escherichia coli* or a bacterium belonging to the genus *Bacillus*; a recombinant DNA comprising the above DNA and a foreign gene, wherein the foreign gene is operably located; a gene expression vector, at least comprising the above DNA; an expression vector comprising the recombinant DNA; a transformant having the above recombinant DNA, or the above expression vector; a method for producing a protein, characterized by culturing the above transformant, and collecting a protein from the resulting culture; and a kit for producing a protein, at least comprising the above DNA, or the above gene expression vector.

13 Claims, 14 Drawing Sheets

HCE II(N) : 5'-cca agc ttg atc tct cct tca cag att cc-3' (29mer)

HCE II(C: T7) :5'-gag gat cca gcc atg gta tat ctc ctt ttt cca gaa gtg tga aa-3' (44mer)

HCE II(N) : 5'-cca agc ttg atc tct cct tca cag att cc-3' (29mer)

HCE II(C:original) : 5'-agg gat cca gcc atg ggt tcc agc tcc ttt ttc cag aa-3' (38mer)

PROMOTERS AND GENE EXPRESSION METHOD BY USING THE PROMOTERS

This application is the national phase under 35 U.S.C. § 371 of PCT International Application No. PCT/JP01/03607 which has an International filing date of Apr. 26, 2001, which designated the United States of America.

TECHNICAL FIELD

The present invention relates to a novel promoter capable of conveniently and inexpensively expressing a desired gene product at a high level, and concretely to an isolated DNA having a sequence of the promoter and a method for producing a protein using the DNA.

BACKGROUND ART

When a useful gene product is produced in a genetically engineering manner, depending upon its purpose, there has been used an expression system using as a host a microbial cell such as *Escherichia coli*, *Bacillus subtilus*, or an yeast; an animal cell, an insect cell, a plant cell or the like of which cultivation means has been established, and using a promoter appropriate for the host. Among them, an expression system using *Escherichia coli* as a host and lac promoter or a derivative thereof or the like is a kind of system which is often used from the viewpoint of its facility in handling.

However, the expression system using lac promoter or a derivative thereof has some defects such that the expression system is industrially disadvantageous because the induction of gene expression is necessitated during expression of the gene product. For instance, lac promoter, tac promoter or the like has some defects such that it is disadvantageous to carry out the above expression on an industrial scale, because expensive IPTG (isopropyl-β-D-thiogalactopyranoside) is required for the induction of gene expression.

On the other hand, an expression vector utilizing temperature induction of phage λ promoter has also been generally used. However, in temperature-induced overexpression of a recombinant gene product, there may be some disadvantages of (a) difficulty for achieving a rapid shift-up of temperature; (b) increase in possibility of the formation of insoluble inclusion bodies at a higher culturing temperature; and (c) induction of some proteases in *Escherichia coli* during heat shock.

Therefore, there has been desired a means which allows highly efficient expression without inducing gene expression.

DISCLOSURE OF INVENTION

An object of the present invention is to provide a DNA, a recombinant DNA, a gene expression vector, an expression vector, and a transformant, all of which have promoter sequence capable of expressing a gene at a high level without inducing gene expression by an inducer; and a method for producing a protein and a kit therefor, which can be operated easily and performed inexpensively by convenient and inexpensive steps.

The gist of the present invention relates to:

[1] an isolated DNA having a nucleotide sequence selected from the group consisting of:
  (A) the nucleotide sequence of SEQ ID NO: 1 or 2;
  (B) a nucleotide sequence having substitution, deletion or addition of at least one residue in SEQ ID NO: 1 or 2;
  (C) a nucleotide sequence of a nucleic acid capable of hybridizing to a nucleic acid consisting of the nucleotide sequence of SEQ ID NO: 1 or 2 under stringent conditions; and
  (D) a nucleotide sequence having at least 80% sequence identity to the nucleotide sequence of SEQ ID NO: 1 or 2, or a fragment thereof, wherein the isolated DNA exhibits a constitutive promoter activity in *Escherichia coli* or a bacterium belonging to the genus *Bacillus*;

[2] the isolated DNA according to item [1] above, wherein the isolated DNA is capable of expressing a foreign gene in the absence of an inducer, when located upstream from the gene;

[3] a recombinant DNA comprising the DNA of item [1] or [2] above and a foreign gene, wherein the foreign gene is operably located;

[4] the recombinant DNA according to item [3] above, wherein the foreign gene is a nucleic acid selected from the group consisting of a nucleic acid encoding a protein, a nucleic acid encoding antisense RNA, and a nucleic acid encoding a ribozyme;

[5] a gene expression vector, at least comprising the DNA of item [1] or [2] above;

[6] the gene expression vector according to item [5] above, wherein the vector is a vector selected from the group consisting of plasmid vectors, phage vectors and viral vectors;

[7] the gene expression vector according to item [5] or [6] above, which comprises the nucleotide sequence of SEQ ID NO: 3 or 4.

[8] an expression vector comprising the recombinant DNA of item [3] or [4] above;

[9] the expression vector according to item [8] above, wherein the vector is a vector selected from the group consisting of plasmid vectors, phage vectors and viral vectors;

[10] a transformant having the recombinant DNA of item [3] or [4] above, or the expression vector of item [8] or [9] above;

[11] a method for producing a protein, characterized by culturing the transformant of item [10] above, and collecting a protein from the resulting culture; and

[12] a kit for producing a protein, at least comprising the DNA of item [1] or [2] above, or the gene expression vector of any one of items [5] to [7] above.

BEST MODE FOR CARRYING OUT THE INVENTION

Figure 1:
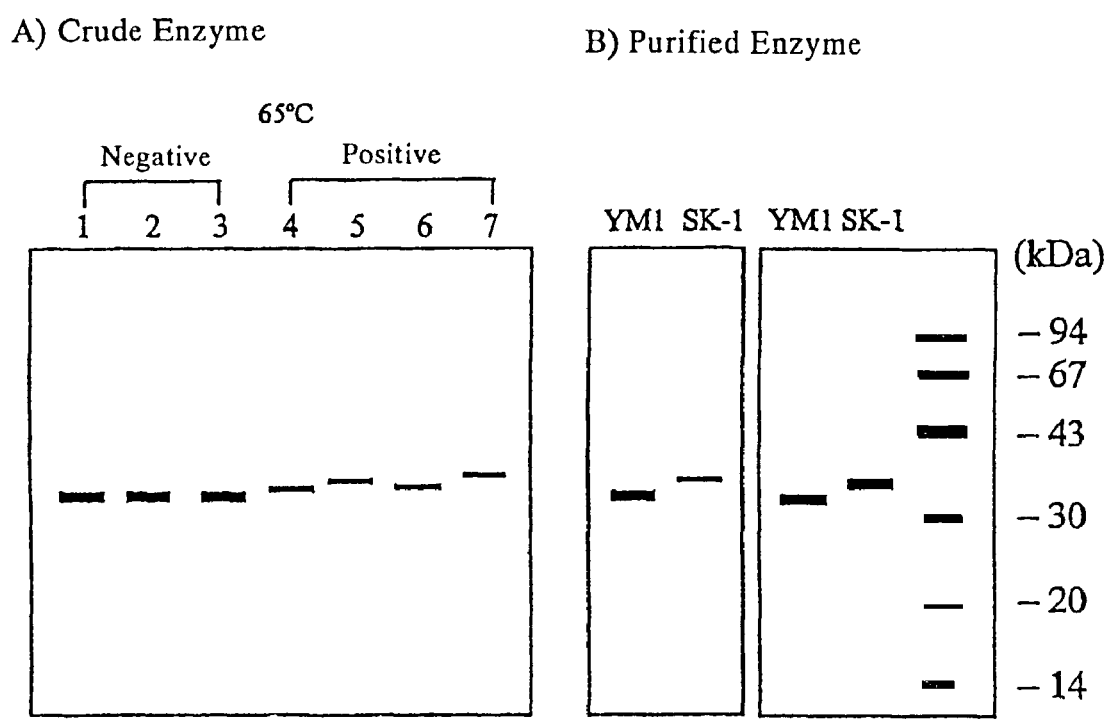
FIG. 1 is a schematic view showing SDS-PAGE results of a crude enzyme solution and a purified enzyme of a strain screened for D-AAT activity.

The DNA of the present invention is localized upstream from ORF of D-amino acid aminotransferase from *Bacillus* sp. SK-1, and is derived from an element showing a promoter activity. The present invention is based on a surprising finding by the present inventors that when a foreign gene (also referred to as "desired gene") is located downstream from the above-mentioned DNA, the desired gene product can be expressed at a level of at least about 30 to about 50% of total amounts of proteins in the absence of an expression inducer.

The DNA of the present invention includes a DNA having the nucleotide sequence of SEQ ID NO: 1 or 2. More preferred are isolated DNAs each exhibiting a constitutive promoter activity in *Escherichia coli* or a bacterium belonging to the genus *Bacillus*.

In the present specification, the term "promoter" includes to the TATA box or a TATA box-like region, which is located 20 to 30 base pairs upstream from the transcription initiation point (+1) and functions to allow RNA polymerase to initiate transcription from an accurate position, but is not necessarily limited to portions near these regions and may include, in addition to the regions, a region required for association of a protein other than the RNA polymerase for regulation of expression. Also, there may be described as "promoter region" in the present specification, and this term refers to a region containing the promoter in the present specification.

In the present specification, the term "promoter activity" shows that a gene has ability and function for producing an expression product of the gene inside or outside of the host, when the gene is located downstream from the promoter in a manner such that the gene is expressible, and the resulting construct is introduced into a host.

Generally, the above-mentioned "promoter activity" can be assayed by a process comprising the following steps of:
1) ligating the DNA to be determined, to upstream region of a gene encoding a protein which is readily quantified or confirmed (hereinafter also referred to as a "reporter gene");
2) introducing the resulting construct into a host;
3) culturing the resulting transformant, thereby expressing the protein; and
4) determining an expression level of the protein.

In addition, the presence or absence of the "promoter activity" can be determined by, for instance, confirmation of expression of the gene product of the gene inside or outside of the host, when a sequence thought to have a promoter sequence is ligated upstream region from he reporter gene, and the resulting construct is introduced into a host. Here, the case where expression is found is an index such that the promoter has a promoter activity in the introduced host.

In the present specification, the term "constitutive promoter" refers to a promoter by which transcription is performed constantly at a given level irrelevant to the growth conditions. In other words, the "constitutive promoter" is capable of expressing a gene located downstream from the promoter without induction by using an inducer as represented by IPTG or the like.

The DNA of the present invention encompasses a fragment of the above-mentioned isolated DNA having the nucleotide sequence of SEQ ID NO: 1 or 2, as long as the constitutive promoter activity is found. Here, the "fragment" can be appropriately selected within the range so that the constitutive promoter activity is found. The fragment can be selected from the above-mentioned process of the steps 1) to 4). The length of the above-mentioned "fragment" is, for instance, exemplified by those having 500 bases or less.

The DNA of the present invention also encompasses a DNA having a nucleotide sequence having substitution, deletion or addition of at least one base, concretely, one or more bases in the nucleotide sequence of SEQ ID NO: 1 or 2, wherein the DNA has the constitutive promoter activity. Generally, in DNA having a short sequence, although a DNA having mutation (substitution, deletion or addition) in at least one base may show change in its activity, the present invention encompasses "a DNA having mutation" of which constitutive promoter activity is found by the above-mentioned process of the steps 1) to 4). This mutation may be any of naturally occurring mutations and artificially introduced mutations.

As a method for artificially introducing a mutation, there is included conventional site-directed mutagenesis method. As the site-directed mutagenesis method, there can be employed, for instance, a method utilizing amber mutation [gapped duplex method, *Nucleic Acids Research*, 12, pp9441–9456 (1984)]; a method utilizing a host deficient dut (dUTPase) gene and ung (uracil-DNA glycosilase) gene [Kunkel method, *Proceedings of the National Academy of Sciences of the USA*, 82, pp488–492 (1985)]; a method by PCR utilizing amber mutation (WO 98/02535); and the like.

The length of the DNA having mutation may be any length in which the constitutive promoter activity is found by the above-mentioned process of the steps 1) to 4), and is exemplified by, for instance, those having 500 bases or less.

In addition, the present invention encompasses the DNA (a) capable of hybridizing with a strand complementary to the DNA of the present invention under stringent conditions, wherein the DNA has the constitutive promoter activity; or the DNA (b) obtained by using, for instance, oligonucleotide probes or primers which are designed by a conventional method on the basis of the DNA of the present invention and chemically synthesized, preferably an isolated DNA having the constitutive promoter activity in *Escherichia coli* or a bacterium belonging to the genus *Bacillus*. As the DNAs, for instance, there may be selected those in which the constitutive promoter activity is found by the above-mentioned process of the steps 1) to 4). The nucleotide sequence of the oligonucleotide probe is not particularly limited, as long as they are those which are capable of hybridizing to the above-mentioned DNA, or to a DNA having a nucleotide sequence complementary thereto under stringent conditions.

Here, the term "stringent conditions" refers to, for instance, the following conditions. Concretely, in the case of the above-mentioned DNA (a), there are exemplified conditions of carrying out incubation at 50° C. for overnight in a solution containing 6×SSC (wherein 1×SSC is 0.15 M NaCl, 0.015 M sodium citrate, pH 7.0), 0.5% SDS, 5× Denhardt's [0.1% bovine serum albumin (BSA), 0.1% polyvinyl pyrrolidone, 0.1% Ficol 400], and 100 μg/ml salmon sperm DNA. In the case of the above-mentioned DNA (b), there are exemplified conditions of carrying out incubation overnight at a temperature of Tm of the probe used minus(−) 25° C. in the solution similarly prepared as mentioned above.

Also, the nucleotide sequence of the primer is not particularly limited, as long as the primer is annealed to the above-mentioned DNA or a DNA having a nucleotide sequence complementary thereto and allows the DNA polymerase to initiate the extension reaction under usual reaction conditions for PCR.

Tm of the oligonucleotide probe or primer can be calculated, for instance, by the following equation:

$$Tm = 81.5 - 16.6(\log_{10}[Na^+]) + 0.41(\% \ G+C) - (600/N)$$

wherein N is a chain length of the oligonucleotide probe or primer; and % G+C is a content of guanine and cytosine residues in the oligonucleotide probe or primer.

In addition, when the chain length of the oligonucleotide probe or primer is shorter than 18 bases, Tm can be deduced from a sum of a product of the contents of A+T (adenine+thymine) residues multiplied by 2° C., and a product of the contents of G+C residues multiplied by 4° C., [(A+T)×2+(G+C)×4].

The chain length of the above-mentioned oligonucleotide probe is not particularly limited. It is preferable that the chain length is 15 bases or more, more preferably 18 bases or more, from the viewpoint of preventing nonspecific hybridization.

Also, the chain length of the primer is not particularly limited. For instance, it is preferable that the chain length is 15 to 40 bases, preferably 17 to 30 bases. The above-mentioned primer can be used for various gene amplification methods such as PCR method, and the resulting DNA having the constitutive promoter activity is also encompassed in the present invention.

Also, the details of the hybridization manipulations are described, for instance, in *Molecular Cloning: A Laboratory Manual*, 2nd Ed., published by Cold Spring Harbor Laboratory in 1989, edited by T. Maniatis et al.

The length of the above-mentioned DNAs (a) and (b) may be a length in which the constitutive promoter activity is found by the above-mentioned process of the steps 1) to 4). For instance, there may be exemplified those having a length of 500 bases or less.

Also, the DNA of the present invention encompasses a DNA having a nucleotide sequence having at least 80% sequence identity, preferably at least 90% sequence identity, more preferably at least 95% sequence identity to the nucleotide sequence of SEQ ID NO: 1 or 2, wherein the DNA has the constitutive promoter activity. More concretely, a DNA having at least 80% sequence identity, preferably at least 90% sequence identity, more preferably at least 95% sequence identity to the nucleotide sequence of SEQ ID NO: 1, wherein the DNA has the constitutive promoter activity; a DNA having at least 80% sequence identity, preferably at least 90% sequence identity, more preferably at least 95% sequence identity to the nucleotide sequence of SEQ ID NO: 2, wherein the DNA has the constitutive promoter activity; and the like. This DNA may be, for instance, any of those in which the constitutive promoter activity is found by the above-mentioned process of the steps 1) to 4).

The above-mentioned "sequence identity" refers to sequence similarity for residues between the two polynucleotides. The above-mentioned "sequence identity" can be determined by comparing two nucleotide sequences aligned optimally over the region of the nucleotide sequence to be compared. Here, the polynucleotide to be compared may have addition or deletion (for instance, gap, overhang, or the like) as compared to the reference sequence (for instance, consensus sequence or the like) for optimally aligning the two sequences.

The numerical value (percentage) of the sequence identity can be calculated by determining identical nucleic acid bases which are present in both of the sequences to determine the number of matched sites, thereafter dividing the above-mentioned number of the matched site by a total number of bases present within the region of the sequence to be compared, and multiplying the resulting numerical value by 100. An algorithm for obtaining optimal alignment and homology includes, for instance, local homology algorithm by Smith et al. [*Add. APL. Math.*, 2, p482 (1981)], homology alignment algorithm by Needleman et al. [*Journal of Molecular Biology*, 48, p443, (1970)], and homology searching method by Pearson et al. [*Proceedings of the National Academy of Sciences of the USA*, 85, p2444 (1988)]. More concretely, there are included dynamic programming method, gap penalty method, Smith-Waterman algorithm, Good-Kanehisa algorithm, BLAST algorithm, FASTA algorithm, and the like.

The sequence identity between the nucleic acids is determined, for instance, by using a sequence analysis software, concretely BLASTN, FASTA and the like. The above-mentioned BLASTN is generally accessible at homepage address: http://www.ncbi.nlm.nih.gov/BLAST/, and the above-mentioned FASTA is generally accessible at homepage address: http://www.ddbj.nig.ac.jp.

According to the DNA of the present invention, there is also provided a recombinant DNA comprising the DNA of the present invention and a foreign gene, wherein the foreign gene is operably located. The recombinant DNA is also encompassed in the present invention.

In the present specification, a foreign gene is intended to encompass any of a gene derived from a different origin from the organism from which the DNA of the present invention is originated; a gene heterogenous to the DNA of the present invention; or a gene heterogenous to a host when the DNA of the present invention is used by introducing an appropriate host as described below.

The above-mentioned foreign gene is not particularly limited. The foreign gene includes, for instance, a nucleic acid encoding a protein, a nucleic acid encoding antisense RNA, a nucleic acid encoding a ribozyme, and the like. The origin of the foreign gene is not particularly limited. The origin includes, for instance, microorganisms such as bacteria, yeasts, Actinomycetes, filamentous fungi, Ascomycetes, and Basidiomycetes; plants; insects; animals; and the like, and there are also included artificially synthesized genes according to its purpose.

The nucleic acid encoding a protein includes, for instance, nucleic acids encoding enzymes, cytokines, antibodies, and the like. More concretely, the nucleic acid includes, for instance, interleukin 1–12 genes, interferon α, β or γ gene, tumor necrosis factor gene, colony-stimulating factor gene, erythropoietin gene, transforming growth factor-β gene, immunoglobulin gene, tissue plasminogen activator gene, urokinase gene, firefly luciferase gene, and the like, without being limited thereto.

The "ribozyme" in the present specification refers to a substance which cleaves mRNA for particular proteins, and inhibits translation for these particular proteins. The ribozyme can be designed from the sequence of a gene encoding the particular protein. For instance, hammerhead-type ribozyme can be prepared by the method described in *FEBS Letter,* 228, pp228–230 (1988). Also, in addition to the hammerhead-type ribozyme, the ribozyme in the present specification encompasses any of those capable of cleaving mRNA for particular proteins and inhibiting translation of these particular proteins, regardless of the kinds of ribozymes such as hairpin-type ribozymes and delta-type ribozymes.

In the present specification, "the foreign gene is operably (located)" means that the foreign gene is under control of the promoter activity exhibited by the DNA of the present invention.

The method for obtaining a DNA of the present invention includes, for instance, (1) a method of isolation from an organism, as described in Examples set forth below; (2) a method of selection from genomic DNA of an organism using appropriate probes or primers, which are based on the nucleotide sequence of SEQ ID NO: 1 or 2; (3) a chemically synthesizing method on the basis of the nucleotide sequence of SEQ ID NO: 1 or 2; and the like.

When a DNA consisting of the nucleotide sequence of SEQ ID NO: 1 or 2 is prepared by chemical synthesis, the above-mentioned DNA can be synthesized by, for instance, enzymatically ligating oligonucleotides synthesized chemically by conventional phosphoramidite method or the like. Concretely, the DNA can be obtained by, for instance, the following steps:

(1) synthesizing each of several dozen kinds of oligonucleotides $A_n$ (wherein n is a positive integer) which can cover the nucleotide sequence of SEQ ID NO: 1 or 2, and
complementary strand oligonucleotides $a_n$ (wherein n is a positive integer) having the same length as $A_n$, and consisting of a sequence complementary to a nucleotide sequence resulting from a shift with several bases at 3'-side or 5'-side on the $A_n$ sequence, wherein the complementary strand oligonucleotides an are annealed with the oligonucleotides $A_n$, thereby generating double-stranded DNAs having 5'-cohesive end or 3'-cohesive end, by conventional chemical synthesis methods
[For instance, when an oligonucleotide consisting of the nucleotide sequence of SEQ ID NO: 1 is prepared, the above-mentioned $A_n$ are oligonucleotides each consisting of base nos: 1–20 ($A_1$), 21–40 ($A_2$), 41–60 ($A_3$), 61–80 (A4), 81–100 ($A_5$), 101–120 ($A_6$), 121–140 ($A_7$), 141–160 ($A_8$), 161–180 ($A_9$), 181–200 ($A_{10}$), and 201–223 ($A_{11}$) of SEQ ID NO: 1, and
the above-mentioned $a_n$ are strands complementary to oligonucleotides each consisting of base nos: 1–23 ($a_1$), 24–43 ($a_2$), 44–63 ($a_3$), 64–83 ($a_4$), 84–103 ($a_5$), 104–123 ($a_6$), 124–143 ($a_7$), 144–163 (a8), 164–183 (a9), 184-203 ($a_{10}$), and 204-223 ($a_{11}$) of SEQ ID NO: 1.];

(2) phosphorylating each 5'-end of the oligonucleotides $A_n$ and each 5'-end of the corresponding complementary strand oligonucleotides $a_n$, obtained in the step (1) mentioned above, by using ATP and conventional T4 polynucleotide kinase;

(3) annealing each of the oligonucleotides $A_n$ and each of the corresponding complementary strand oligonucleotides $a_n$, obtained in the step (2) mentioned above, thereby giving several dozens of "double stranded DNA ($A_n a_n$) having 5'-cohesive end or 3'-cohesive end";

(4) dividing the double-stranded DNAs ($A_n a_n$) obtained in the step (3) mentioned above into several blocks corresponding to the nucleotide sequence of SEQ ID NO: 1 or 2 in an n-ascending order, and putting the double-stranded DNAs ($A_n a_n$) obtained in the step (3) mentioned above together in one tube corresponding to each block
[For instance, when the oligonucleotide consisting of the nucleotide sequence of SEQ ID NO: 1 is prepared, there are set:
a tube for oligonucleotides $A_1$–$A_4$ and complementary strands $a_1$–$a_4$,
a tube for oligonucleotides $A_5$–$A_8$ and complementary strands $a_5$–$a_8$, and
a tube for oligonucleotides $A_9$–$A_{11}$ and complementary strands $a_9$–$a_{11}$.];

(5) ligating the double-stranded DNAs for every tube in the step (4) mentioned above corresponding to each block, thereby giving double-stranded DNAs corresponding to each block;

(6) subjecting the double-stranded DNAs obtained in the step (5) mentioned above to gel electrophoresis, and extracting from a gel a band for the double-stranded DNA having the desired chain length corresponding to each block;

(7) putting together and ligating the double-stranded DNAs each having the desired chain length corresponding to each block obtained in the step (6) mentioned above; and (8) examining the chain length on gel electrophoresis and/or performing nucleotide sequencing for the DNA obtained in the step (7) mentioned above, thereby confirming that the resulting DNA is DNA consisting of the nucleotide sequence of SEQ ID NO: 1 or 2.

Since the DNA of the present invention is a promoter which is capable of expressing the gene at a high level without inducing gene expression, the DNA is especially suitable for expression of a foreign gene, which is a nucleic acid encoding a protein.

Also, according to the DNA of the present invention, there is provided a gene expression vector at least comprising the DNA. The gene expression vector is also encompassed in the present invention.

According to the gene expression vector, since the vector comprises the DNA of the present invention, the desired gene product can be constitutively expressed on the level of at least about 30 to about 50% of total amounts of intracellular protein produced by the host, and the desired gene product can be easily expressed depending upon its purposes and the like.

Figure 5:
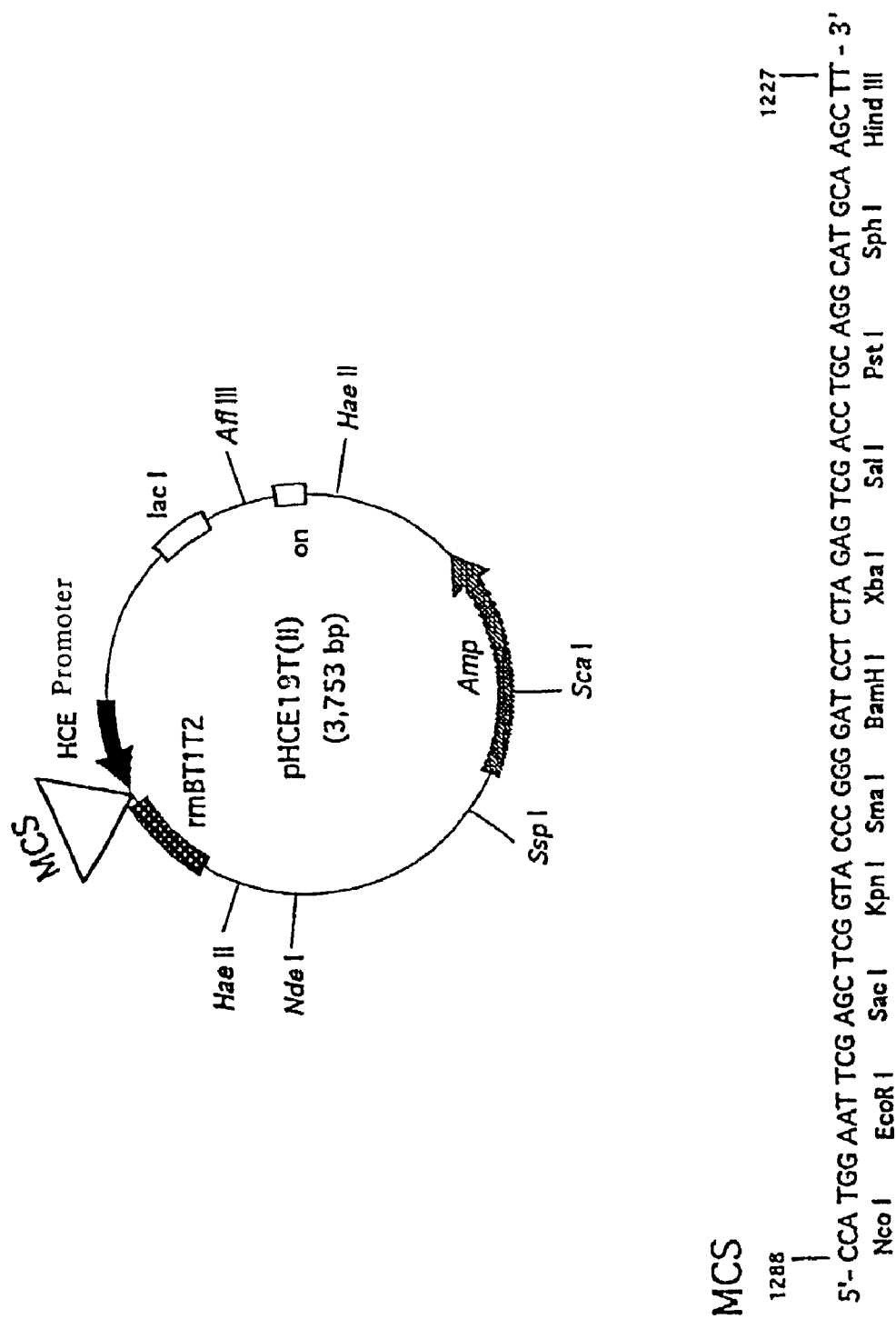
FIG. 5 is a schematic view showing the gene expression vector pHCE19T(II). MCS Sequence=SEQ ID NO:10.
Figure 7:
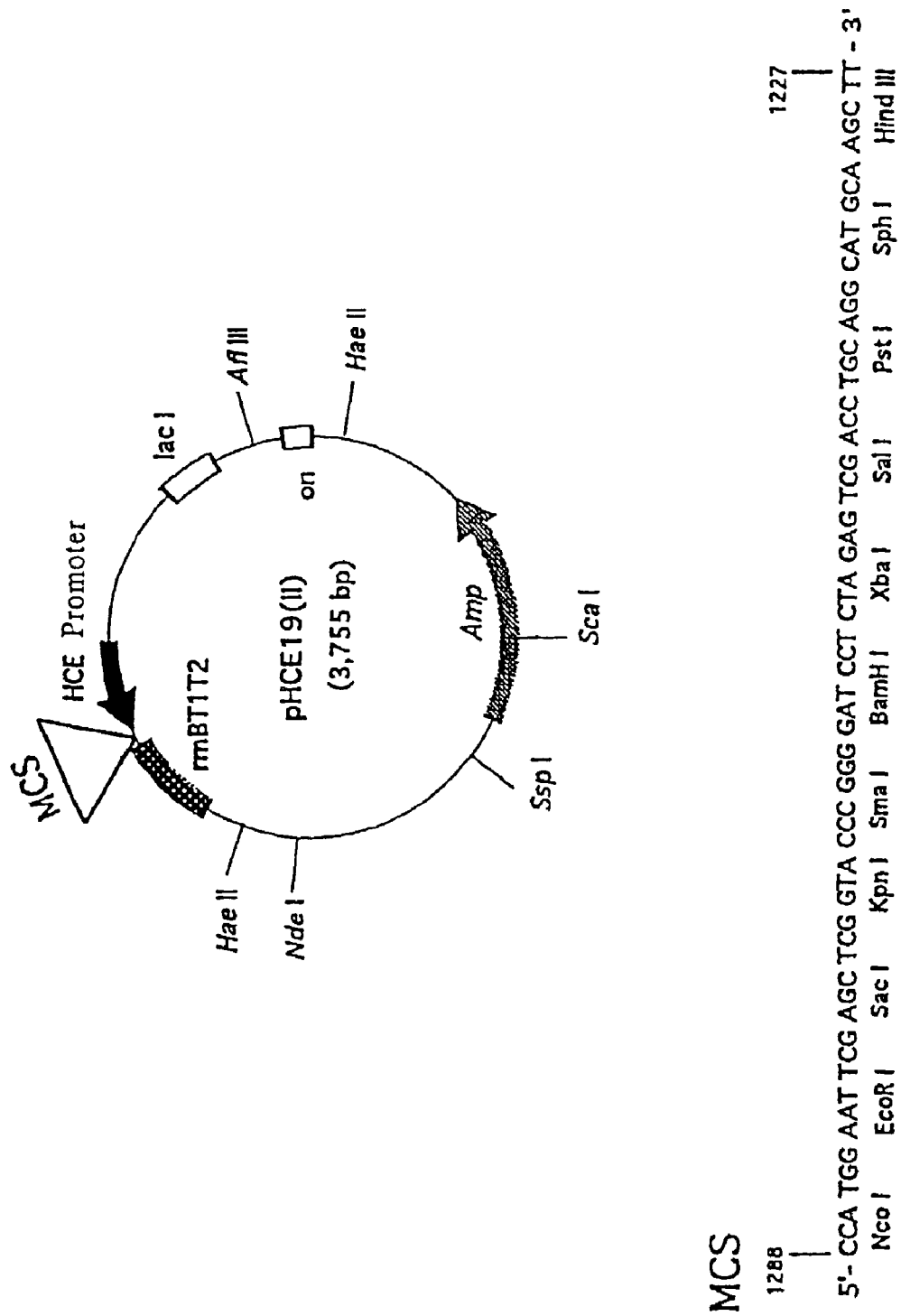
FIG. 7 is a schematic view showing the gene expression vector pHCE19(II). MCS Sequence=SEQ ID NO:10.

Concrete examples of the gene expression vector of the present invention include pHCE19T(II) [FIG. 5], and pHCE19(II) [FIG. 7].

Incidentally, *Escherichia coli* JM109 transformed with the above-mentioned plasmid pHCE19T(II) was named and represented as *Escherichia coli* JM109/pHCE19T(II) and deposited under the Budapest Treaty with the accession number of FERM BP-7535 with the International Patent Organism Depositary, National Institute of Advanced Industrial Science and Technology, of which the address is AIST Tsukuba Central 6, 1-1, Higashi 1-chome, Tsukuba-shi, Ibaraki-ken 305-8566, Japan, since Apr. 14, 2000 (original date of deposit). Also, *Escherichia coli* JM109 transformed with the above-mentioned plasmid pHCE19 (II) was named and represented as *Escherichia coli* JM109/pHCE19(II) and deposited under the Budapest Treaty with the accession number of FERM BP-7534 with the International Patent Organism Depositary, National Institute of Advanced Science and Technology, of which the address is AIST Tsukuba Central 6, 1-1, Higashi 1-chome, Tsukuba-shi, Ibaraki-ken 305-8566, Japan, since Apr. 14, 2000 (original date of deposit). pHCE19T(II) and pHCE19(II), which are one of examples of the gene expression vectors of the present invention can also be made available from deposited *Escherichia coli*.

In the gene expression vector of the present invention, a vector includes plasmid vectors, phage vectors, and viral vectors. The above-mentioned vector can be appropriately selected depending upon the cell which is used as a host.

The cell which can be used as a host includes *Escherichia coli* or a bacterium belonging to the genus *Bacillus*. Concretely, the *Escherichia coli* includes HB101 strain, C600 strain, JM109 strain, DH5α strain, DH10 B strain, XL-1BlueMRF' strain, TOP10F strain and the like of the lineage of *Escherichia coli* K-12. Also, the bacterium belonging to the genus *Bacillus* includes *Bacillus* sp., *Bacillus subtilis*, *Bacillus stearothermophilus*, and the like, without being limited thereto. Those obtained by mutation treatment and the like of these *Escherichia coli* or bacteria belonging to the genus *Bacillus* can also be used as a host.

The above-mentioned vector includes, for instance, when the host is *Escherichia coli*, a plasmid vector including pUC18, pUC19, pBluescript, pET, and the like, and a phage vector including lambda phage vectors such as λgt10 and λgt11, and the like.

For the construction of the gene expression vector of the present invention, there can be utilized techniques described in the above-mentioned *Molecular Cloning: A Laboratory Manual*, 2nd Ed., and the like. For instance, the vector can be prepared in accordance with the scheme for the construction shown in FIG. 4. In other words, a DNA fragment (350 bp) comprising 5'-promoter located upstream region of D-AAT gene from thermophilic *Bacillus* sp. SK-1 and SD (Shine-dalgano) sequence is amplified by PCR method using the following primers [primer 1 (SEQ ID NO: 5) and primer 2 (SEQ ID NO: 6)]:
primer 1 (5'ccaagcttgatctctccttcacagattcc-3')(29 mer) and
primer 2 (5'gaggatccagccatggtatatctccttttccagaagtgtgaaa-3')(44 mer)

Figure 6:
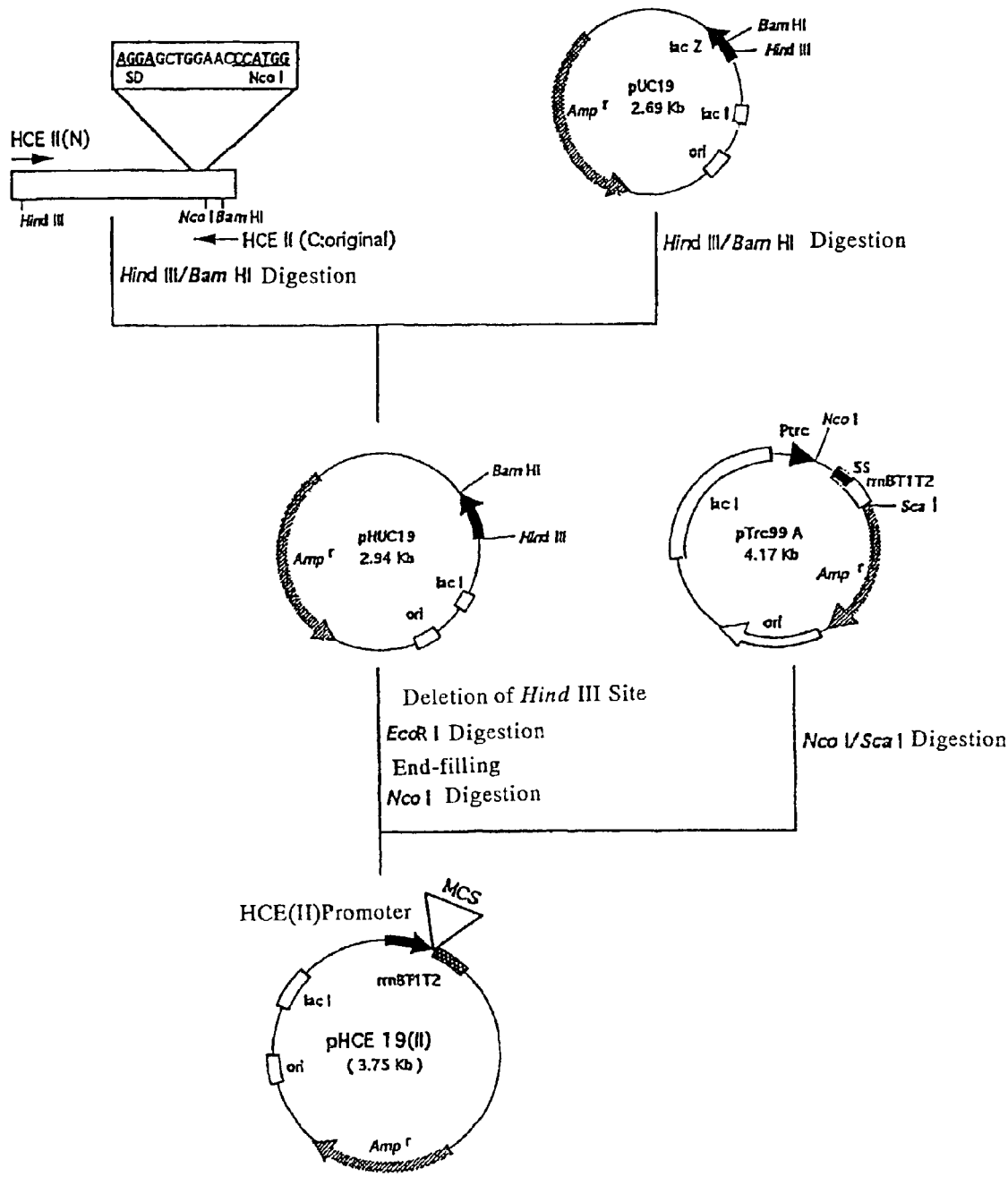
FIG. 6 is a schematic view of a construction of the gene expression vector pHCE19(II). HCE II (N)=SEQ ID NO:5. HCE II (C:original)=SEQ ID NO:7.

Next, the amplified fragment containing promoter is digested with HindIII and BamHI, and the resulting product is purified. The resulting fragment is ligated to a larger fragment of HindIII- and BamHI-digested pUC19, to prepare pHUC19T. Subsequently, an NcoI-ScaI fragment containing potent transcription terminator rrnBT1T2 derived from an expression vector pTrc99A is inserted into an NcoI-EcoRI (filling-in) site on pHUC19T, whereby a gene expression vector pHCE19T(II) can be obtained (FIG. 5). The sequence of the promoter region can be confirmed by DNA nucleotide sequencing. Also, the same procedures are carried out using the following primer 3 (SEQ ID NO: 5):
primer 3 (5'-agggatccagccatgggttccagctccttttccagaa-3')(38 mer)
in place of primer 2, whereby the gene expression vector pHCE19(II) having a length different from that between SD sequence and NcoI site can be obtained (FIGS. 6 and 7).

Also, the above-mentioned pHCE19(II) can be obtained by mutating the nucleotide sequence: 5'-gatata-3', which is located between SD sequence and NcoI site of pHCE19T (II), to 5'-gctggaac-3' by known mutagenesis method.

The gene expression vector of the present invention may contain a terminator such as rrnBT1T, a selectable marker gene, and the like.

The selectable marker includes ampicillin-resistant gene, kanamycine-resistant gene, chloramphenicol-resistant gene, and the like.

In addition, the gene expression vector of the present invention may contain, depending on its purpose of the desired gene product, for instance, for simplification of the isolation procedure of the desired gene product, a sequence which allows to be expressed as a fusion protein with a heterologous protein such as glutathione-S-transferase and maltose-binding protein, or a tag sequence which allows to be expressed as a protein to which histidine tag or the like is added.

The gene expression vector of the present invention includes, for instance, a vector having the nucleotide sequence of SEQ ID NO: 3 or 4.

Further, according to the present invention, there is provided an expression vector comprising the above-mentioned recombinant DNA. The expression vector is also encompassed in the present invention. In addition, the expression vector of the present invention encompasses a construct obtained by incorporating a desired gene into the above-mentioned gene expression vector.

The same vectors as those vectors listed as the above-mentioned gene expression vector can be used.

The expression vector of the present invention can be prepared by (a) incorporating the above-mentioned recombinant DNA into an appropriate vector, and (b) incorporating a desired gene to the above-mentioned gene expression vector.

Also, according to the recombinant DNA and the expression vector of the present invention, there can be provided a transformant harboring the above-mentioned recombinant DNA, or a transformant harboring the above-mentioned expression vector.

The host includes the same cells as the previously mentioned "cell(s) which can be used as a host."

The introduction of the recombinant DNA into a host can be carried out, for instance, by the methods described in the literatures [*Virology*, 52, p456 (1873), *Molecular and Cellular Biology*, 7, p2745 (1987), *Journal of the National Cancer Institute*, 41, p351 (1968), *EMBO Journal*, 1, p841 (1982)].

The introduction of the expression vector into a host can be carried out, for instance, by calcium phosphate method [*Molecular and Cellular Biology*, 7, p2745 (1987)], electroporation method [*Proceedings of the National Academy of Sciences of the USA*, 81, p7161 (1984)], DEAE-dextran method [*Methods in Nucleic Acids Research*, p283, Edit. by Callam, published by CRC Press, 1991], liposome method [*BioTechniques*, 6, p682 (1989)]; and the like.

Further, according to the transformant of the present invention, there is provided a method for producing a protein, characterized by culturing the transformant, and collecting a protein from the resulting culture. This "method for producing a protein" is also encompassed in the present invention.

More concretely, a protein can be produced by the steps of:

(I) transforming a host cell using:
   a) a recombinant DNA in which a nucleic acid encoding a protein is located downstream from the DNA of the present invention in an expressible state; or
   b) a vector comprising the recombinant DNA; and
(II) culturing the transformant obtained in (I) under conditions appropriate for expression of a protein, and collecting the protein from the culture.

The culture conditions of the transformant can be appropriately selected depending upon the characteristics of the cell used as a host and the protein to be expressed.

The resulting protein can be purified by a conventional protein purification means. The purification means include, for instance, salting-out, ion exchange chromatography, hydrophobic chromatography, affinity chromatography, gel filtration chromatography, and the like.

In the method for producing a protein of the present invention, there can be used a kit for producing a protein, comprising the DNA of the present invention or the gene expression vector of the present invention. According to the kit, the method for producing a protein can be more conveniently carried out.

The present invention will be described in detail by means of Examples, without intending to limit the present invention thereto.

EXAMPLE 1

Screening and Characterization of D-Amino Acid Aminotransferase-Producing Thermophilic Bacteria In order to obtain biocatalysts useful for enzymatic synthesis of D-amino acid and industrial production of D-amino acid, D-amino acid aminotransferase activity (D-AAT) was analyzed for the 1,300 kinds of thermophilic bacteria isolated from the soil of Korea.

The D-ATT activity was determined by measuring the rate of pyruvate formation from D-alanine and α-ketoglutarate. The amount of pyruvate was determined by the coupling method with lactate dehydrogenase or by the salycylaldehyde method [*Analytical Biochemistry*, 27, pp1659–1660 (1995); *Methods in Enzymology*, 113, p108(1985)].

In a determination of the activity, a reaction mixture containing 50 mM pyridoxal-5'-phosphate, 100 mM D-alanine and 100 mM α-ketoglutarate in 100 mM Tris-HCl (pH 8.5) was used. In the case of lactate dehydrogenase (LDH)-coupling assay, 0.3 mM NADH and 5 units/ml LDH were included thereto. One unit of the enzyme activity was defined as the amount of the enzyme catalyzing the formation of 1 mmol of pyruvate per minute. The protein concentration was determined by means of the Bradford method [*Analytical Biochemistry*, 72, pp248–254 (1976)] using bovine serum albumin as a standard.

As a result of searching for the D-AAT activity derived from thermophilic bacteria isolated from various environments, 110 strains of D-AAT-producing bacteria were obtained. Most of them were thought to belong to the genus *Bacillus*, since they were grown under aerobic conditions and formed endospores.

Subsequently, the D-AAT-producing strain was compared for their enzyme activity and thermal stability. As a result, four thermophilic bacteria: two thermophilic bacteria each having higher specific activity, *Bacillus* sp. LK-1 and LK-2, and two thermophilic bacteria each having higher thermal stability than the above-mentioned D-ATT-producing strains, *Bacillus stearothermophilus* KL-01 and *Bacillus* sp. SK-1 were selected as the strains producing proteinous biocatalysts for production of D-amino acid. Two strains LK1 and LK2 each showing the highest D-AAT activity in the D-AAT activity-positive strains, were subjected to taxonomic identification, and it is found that the morphological and biochemical characteristics of the above-mentioned strains were shown to be very similar to those of YM1 strain [*Kor. J. Microbiol. Biotechnol.*, 27, pp184–190 (1999)]. In particular, unlike YM1 strain, the above-mentioned two strains could not grow at 65° C. In Western blot analysis of D-AATs derived from different *Bacillus*, the LK1 enzyme and LK2 enzyme showed strong interaction with the antibody against YM1 D-AAT, and the mobilities of the two isolated D-AATs are the same as that of the D-AAT derived from YM1 (molecular weight: approximately 31 kDa) (FIG. 1).

On the other hand, D-AATs derived from the thermophilic *Bacillus* strains capable of growing at 65° C. showed relative weak immunoblot signals, and the mobility of D-AAT was clearly distinct from that of YM1 D-AAT, which showed molecular weight of 32–34 kDa on SDS-polyacrylamide gel electrophoresis analysis (FIG. 1). The D-AAT activity of the *Bacillus* strains capable of growing at 65° C. was less than 0.02 units/mg protein, which was approximately one-fifth of the D-AAT activities each of LK1 and LK2 [*Kor. J. Microbiol. Biotechnol.*, 27, pp184–190 (1999)]. In order to clarify the characteristics of D-AATs derived from *Bacillus* group capable of growing at 65° C., in this experiment, SK-1 strain was selected as the source of D-AAT.

EXAMPLE 2

Characterization of Thermostable D-Amino Acid Aminotransferase-Producing Thermophilic *Bacillus* sp. SK-1

Isolated *Bacillus* sp. SK-1 had an obligately symbiotic interaction with *Symbiobacterium toebii*. The characteristics of the above-mentioned SK-1 strain are shown as follows:
Bacteriological Characteristics
Aerobic, gram-positive, a motile bacillus
GC content of genomic DNA: 43.9 mol %
Optimum growth conditions
   Temperature: 45–70° C. (optimum temperature: 60° C.)
   pH: 6.0–9.0 (optimum pH: pH 7.5)
Presence of meso-diamino pimelic acid in the cell wall
Presence of branched-chain fatty acids iso-15:0 and iso-17:0 as main cellular fatty acids
Main isoprenoid quinone: MK-7
Comparative sequence analysis of 16S ribosomal DNA
   Closely related to *Bacillus thermoglucosidasius*

EXAMPLE 3

Gene Cloning and Characterization of Thermostable D-Amino Acid Aminotransferase Derived from *Thermophilic Bacillus* sp. SK-1

1) Bacterial Strain and Plasmids
*Bacillus* sp. SK-1 was cultured in MY medium [composition: 1.5% polypeptone, 0.2% yeast extract, 0.2% meat extract, 0.2% glycerol, 0.2% $K_2HPO_4$, 0.2% $KH_2PO_4$ and 0.026% $NH_4Cl$ (pH 7.0)] under aerobic conditions at 60° C. In order to clone the D-AAT gene, *Bacillus* sp. SK-1 (symbiotic bacterium of obligately symbiotic thermophilic bacterium *Symbiobacterium toebii* SC-1) was used as the DNA source. *Escherichia coli* strain WM335 [leu, pro, his, arg, thyA, met, lac, gal, rspL, hsdM, hsdR, murI] (an auxotrophic strain for D-glutamic acid) was employed as the host for gene complementation [*Journal of Bacteriology*, 114, pp499–506 (1978)]. If necessary, *Bacillus* sp. SK-1 was cultured in Luria-Bertani medium supplemented with ampicillin (100 mg/ml) and D-glutamic acid (100 mg/ml).

Plasmids pBluescript II SK and pBluescript II KS were purchased from Stratagene. Plasmids pUC118 and pUC119 were purchased from Takara Shuzo Co. Ltd. *Escherichia coli* XL1-Blue (manufactured by Stratagene) was used as a host strain for subcloning and sequencing of the D-AAT gene.

2) Gene Cloning of D-AAT Derived from *Bacillus* sp. SK-1

Genomic DNA of *Bacillus* sp. SK-1 was prepared as described by Saito et al. [*Biochimica et Biophysica Acta*, 72, pp619–629 (1963)], and thereafter the resulting DNA was partially digested with Sau3AI. DNA fragments of 3–10 kb were isolated by centrifugation on sucrose gradient [5–40% (w/v)] in Beckman SW40 rotor at 25,000 rpm for 20 hours. Then, the resulting fragments were ligated with BamHI-digested pUC118 by using T4 DNA ligase for 12 hours at 16° C. The resulting legation mixture was used to transform the D-glutamate-dependent auxotrophic strain (*Escherichia coli* WM335) by electroporation. Thus, a genomic DNA library of *Bacillus* sp. SK-1 was obtained. From the genomic DNA library, 35 colonies each showing D-glutamic acid-independency and ampicillin resistance were obtained by the complementation for WM335.

The plasmid DNA from each colony was purified by using JetStar 2.0 Plasmid Midi Purification Kit (manufactured by Genomed Co.).

Using isolated plasmids, *Escherichia coli* XL1-Blue cells were transformed. Thereafter, the transformants were cultured, and the resulting cells were assayed for D-AAT activity in the same manner as in Example 1.

Figure 2:
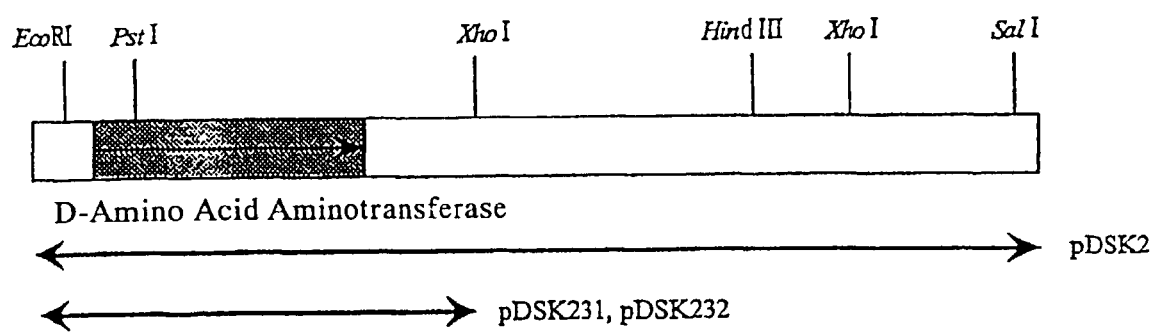
FIG. 2 is a view showing the results of restriction analysis of D-AAT gene from *Bacillus* sp. SK-1.

Among of 12 clones showing D-AAT activity, one clone (pDSK2) showing the highest D-AAT activity [35 units/mg protein (activity in 1750-folds higher than that of cell-free extract from *Bacillus* sp. SK-1 showing 0.02 units/mg protein)] contained a 3.6 kb insert. In order to subclone the D-AAT gene, plasmid pDSK2 was subjected to restriction analysis. As a result, the D-AAT activity for pDSK2 was found to be attributed to the 1.7 kb EcoRI-XhoI fragment (FIG. 2). The above-mentioned 1.7 kb fragment was subcloned into pbluescript II SK and pbluescript II KS, to construct pDSK231 and pDSK232, respectively. The plasmid pDSK232 containing the insert in the opposite direction to pDSK1 showed D-AAT activity at the same level thereto, indicating that this gene was constitutively expressed by its own promoter.

The nucleotide sequence of the D-AAT gene derived from *Bacillus* sp. SK-1 was determined using the PRISM kit (manufactured by Perkin Elmer) and Applied Biosystems 373A DNA sequencer by primer walking on the both DNA strands. Starting primers were pBluescript II SK universal primer and reverse primer, and the primers specific to the internal sequence were synthesized by Korea Biotech (Korea). The sequences determined were analyzed by using Software GENETIX-MAC (S.D.S).

3) Purification

*Escherichia coli* XL1-Blue cells harboring pDSK2 were cultured in LB medium (1 liter) containing 100 mg/ml ampicillin at 37° C. for 16 hours. The resulting cells were collected by centrifugation. The collected cells subsequently were suspended in 50 ml of standard buffer [30 mM Tris-HCl (pH 8.0) containing 0.01% β-mercaptoethanol in final concentration and 20 mM pyridoxal-5'-phosphate (PLP) in final concentration]. The resulting suspension was homogenized by using Sonifier 450 [manufactured by Brason Ultrasonics] on ice with 20% efficiency for 10 minutes. After centrifugation at 15,000 rpm for 60 minutes, the supernatant was collected and heat-treated at 60° C. for 20 minutes. Protein aggregates were removed by centrifugation at 15,000 rpm for 10 minutes.

The resulting supernatant was subjected to Resource Q anion-exchange column (manufactured by Pharmacia) equilibrated with the above-mentioned standard buffer. Proteins were eluted with a linear gradient of 0–1 M NaCl. The fractions showing D-AAT activity were pooled and concentrated by ultrafiltration (manufactured by Amicon). The resulting protein solution was treated so as to contain 1.7 M ammonium sulfate and applied to Phenyl-Superose column (manufactured by Pharmacia) equilibrated with the standard buffer containing 1.7 M ammonium sulfate. Protein was eluted with a linear gradient of 1.7-0 M ammonium sulfate. The fractions having D-AAT activity were collected and concentrated. Thereafter, the resulting concentrate was dialyzed against the standard buffer. The resulting fraction was stored in the deep freezer (at −80° C.). All column procedures were performed by the FPLC system (manufactured by Pharmacia) at room temperature.

Figure 3:
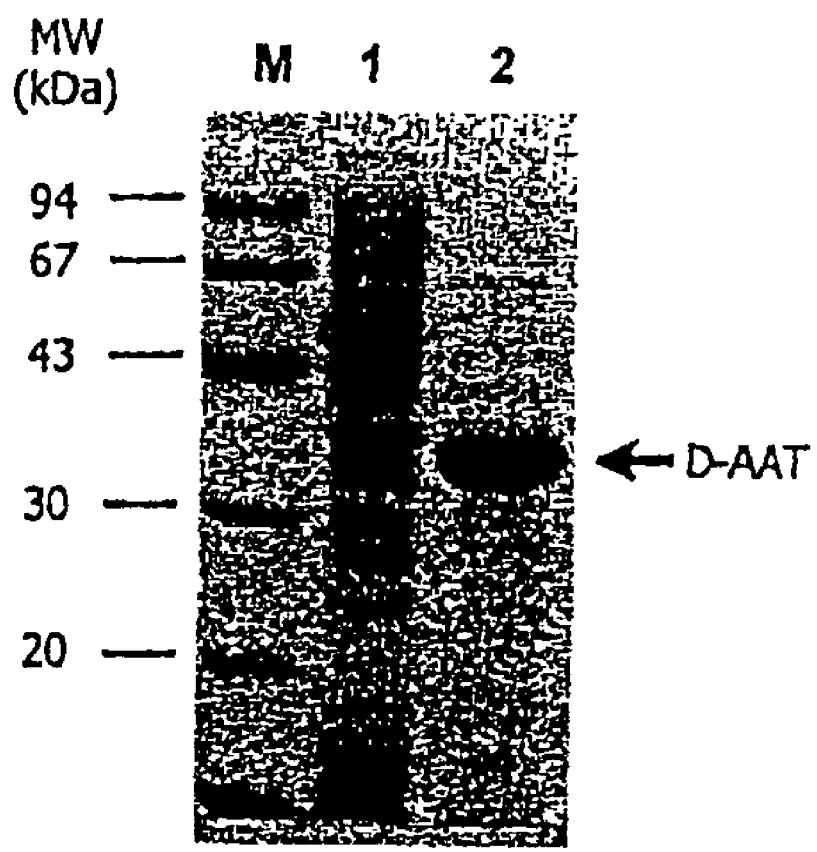
FIG. 3 is a view showing the results of SDS-PAGE analysis of D-AAT gene product from *Bacillus* sp. SK-1.

The fraction obtained from *Escherichia coli* XL1-Blue harboring plasmid pDSK2 revealed a very thick band of protein of a molecular weight 34 kDa (FIG. 3). The amount of the 34 kDa-band was quantified by using an image analyzing system (manufactured by Biorad). As a result, it was shown that the amount of the expressed protein was approximately 60% of the total *Escherichia coli* proteins.

EXAMPLE 4

Construction of Constitutive Expression System (Gene Expression Vector)

In order to construct a gene expression vector capable of constitutively expressing a foreign gene, there were used enzymes for gel purification and plasmid purification and kits for gel purification and plasmid purification, which were commercially available. Unless otherwise specified, the plasmids were constructed according to conventional techniques as described in, for example, T. Maniatis et al. (eds.), *Molecular Cloning: A Laboratory Manual*, 2nd ed, and the like.

Figure 4:
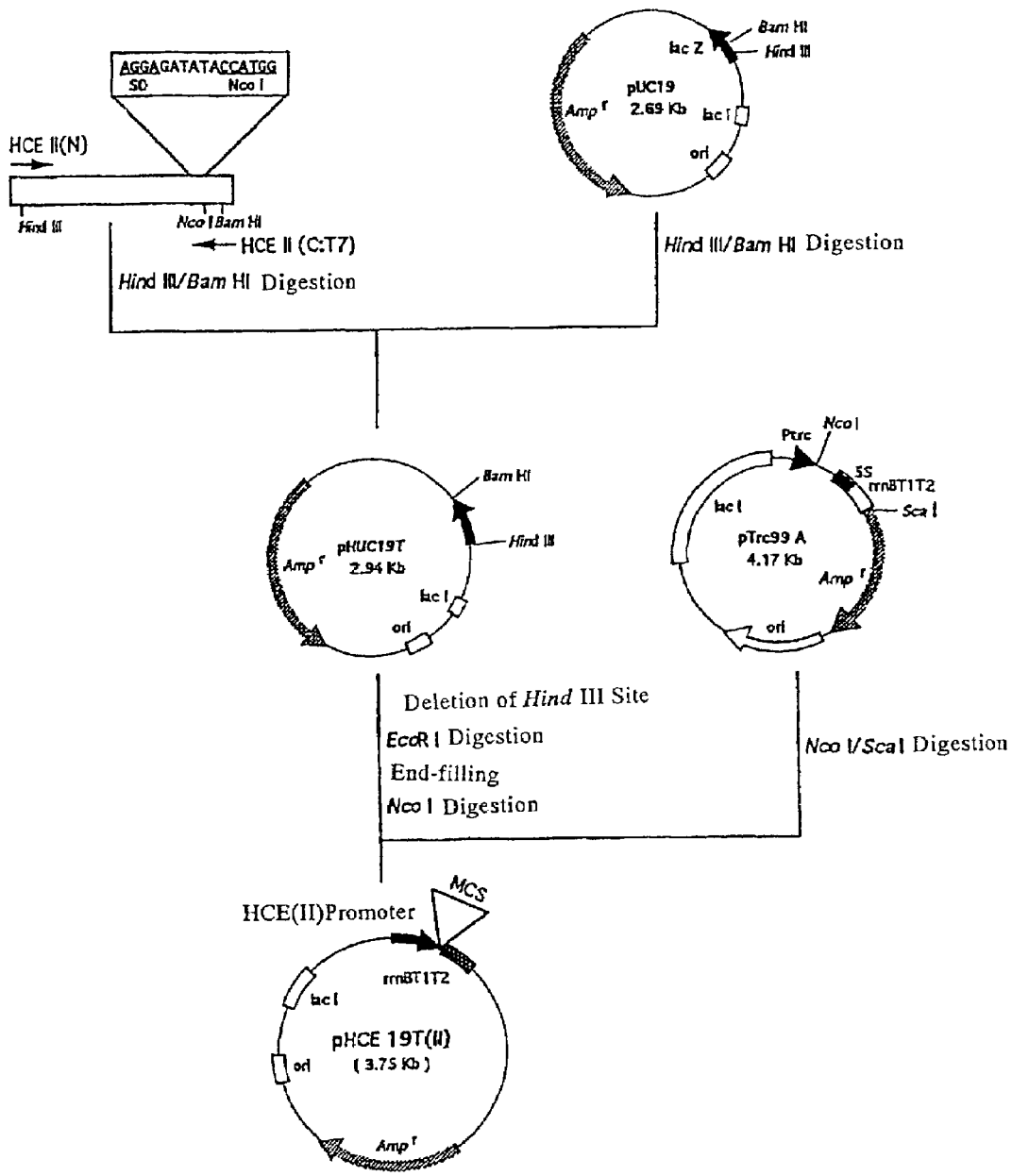
FIG. 4 is a schematic view of a construction of the gene expression vector pHCE19T(II). HCE II (N) SEQ ID NO:5. HCE II (C:T7)=SEQ ID NO:6.

Scheme of construction of the gene expression vector pHCE19T(II) is shown in FIG. 4. A DNA fragment (350 bp) containing 5'-promoter and SD (Shine-Dalgarno) sequence of upstream region from the above-mentioned D-AAT gene from thermophilic *Bacillus* sp. SK-1 was amplified by PCR using the following primers [primer 1 (SEQ ID NO: 5) and primer 2 (SEQ ID NO: 6)]:

primer 1 (5'-ccaagcttgatctctccttcacagattcc-3')(29 mer)

primer 2 (5'-gaggatccagccatggtatatctccttttccagaagtgtgaaa-3') (44 mer).

The amplified fragment containing the promoter was digested with HindIII and BamHI, and thereafter, the resulting product was purified. The resulting fragments were ligated to the larger fragment in HindIII- and BamHI-digested pUC19, to produce pHUC19T. Subsequently, the NcoI-ScaI fragment containing a potent transcription terminator rrnBT1T2 derived from expression vector pTrc99A was inserted into the NcoI-EcoRI (filling-in) site of pHUC19T, to obtain gene expression vector pHCE19T(II) (FIG. 5). Incidentally, the sequence of the promoter region was confirmed by DNA sequencing.

In addition, the gene expression vector pHCE19(II) which is 2 b longer in the length between SD sequence and the NcoI site, was obtained by using the following primer 3 (SEQ ID NO: 7):

primer 3 (5'-agggatccagccatgggttccagctccttttccagaa-3') (38 mer)

in place of primer 2 (FIGS. 6 and 7), in the same manner as described above.

The nucleotide sequence of the gene expression vector pHCE19T(II) produced in the described above is shown in SEQ ID NO: 3 of Sequence Listing, and the 223 bp portion corresponding to the promoter region located upstream from the translation initiation codon ATG is shown in SEQ ID NO: 1 of Sequence Listing.

In addition, the nucleotide sequence of gene expression vector pHCE19(II) produced as the same manner is shown in SEQ ID NO: 4 of Sequence Listing, and the 225 bp portion corresponding to the promoter region located upstream from the translation initiation codon ATG is shown in SEQ ID NO: 2 of Sequence Listing.

EXAMPLE 5

Large-Scale Production of Tryptophan Indole-Lyase Using Constitutive Expression System In this example, using the above-mentioned pHCE19T (II), large-scale production in *Escherichia coli* cells was attempted by cloned TNA gene for tryptophan indole-lyase (hereinafter also referred to as "TNA") derived from thermophilic bacterium *Symbiobacterium toebii* SC-1. In addition, in order to maximize the TNA production using a batch culture system, culture conditions for recombinant *Escherichia coli* cells were studied.

1) Construction of Constitutive Expression Vector Having TNA Gene

Figure 8:
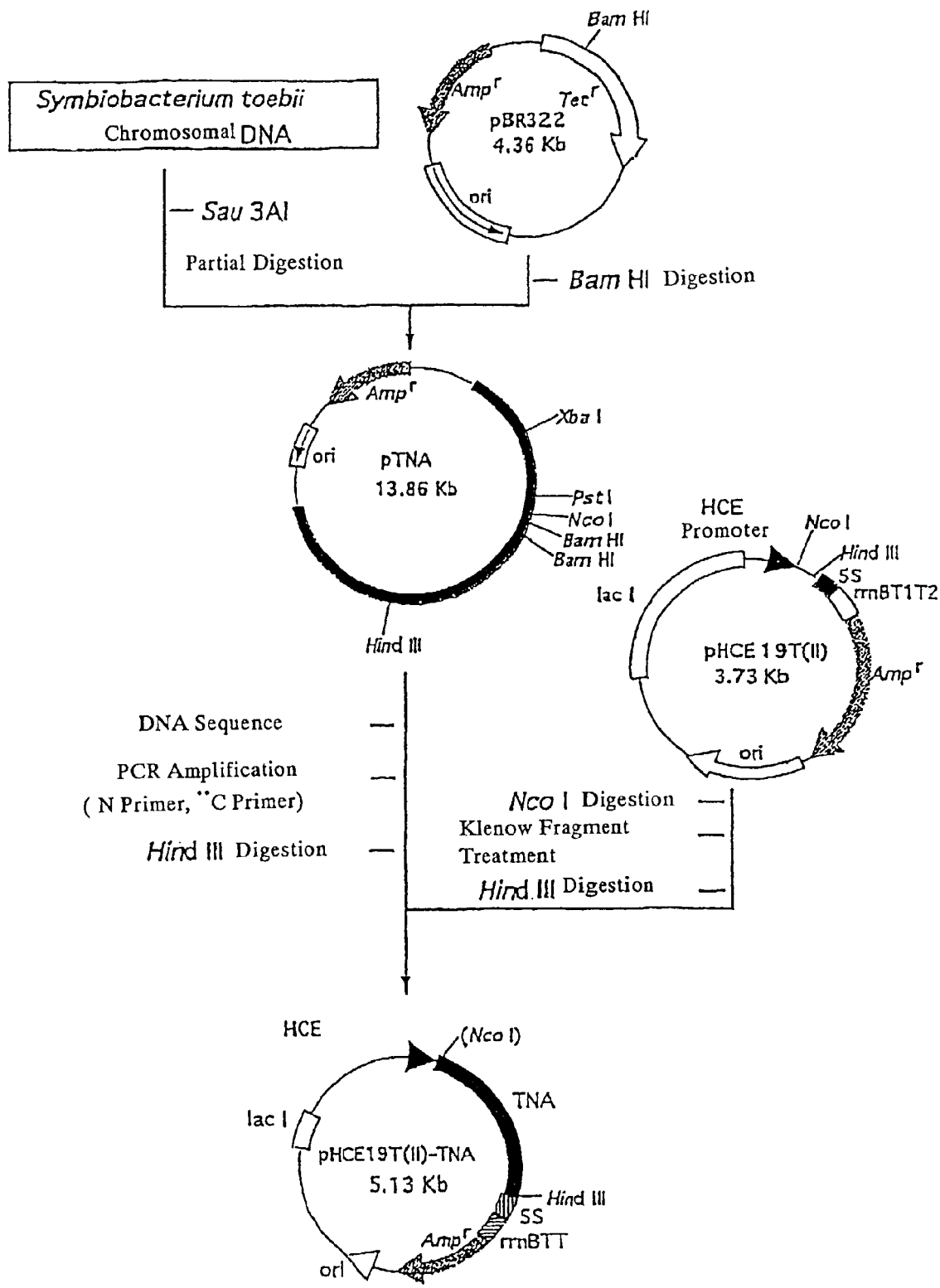
FIG. 8 is a schematic view of a construction of the expression vector pHCE19T(II)-TNA for expressing TNA.

As shown in the strategy described in FIG. 8, the constitutive expression vector pHCE19T(II)-TNA carrying the TNA gene derived from *Symbiobacterium toebii* SC-1 was prepared using the pHCE19T(II) described above.

The TNA gene was amplified by PCR using as a template the pTNA carrying the TNA gene. The primers used are as follows:

N-terminal primer: 5'-ccaaagggcgagccctttaa-3' (20 mer) (SEQ ID NO: 8)

C-terminal primer: 5'-tgactaagtctgcagaagcttattagaccagatcgaagtgcgc-3 (43 mer) (SEQ ID NO: 9).

The amplified TNA gene was digested with HindIII, and thereafter, the resulting product was purified. The pHCE19T (II) was digested with NcoI, and thereafter, the ends were filled in with the Klenow fragment, followed by redigestion with HindIII. The resulting TNA gene was ligated to the larger fragment in the above pHCE19T(II), to obtain pHCE19T(II)-TNA.

2) Preparation of Transformants

Using Gene Pulser system (manufactured by Bio-Rad), *Escherichia coli* HB101[supE44, hsd20(rB- mB-), recA13, ara-14, proA2, lacY1, galK2, rpsL20, xyl-5, mtl-1, leuB6, thi-1] as a host was transformed with the above-mentioned pHCE19T(II)-TNA.

Transformants were cultured in LB medium containing 10 g/l tryptophan (manufactured by Difco), 5 g/l yeast extract (manufactured by Difco) and 10 g/l sodium chloride.

3) Preparation of Enzyme Solution

The transformants obtained in the above-mentioned item 2) were collected by centrifugation at 5,000×g for 20 minutes, and the resulting cells were washed with 50 mM potassium phosphate buffer (pH 8.5). The resulting cells were suspended in 50 mM potassium phosphate buffer (pH 8.5) containing 0.1 mM PLP and 10 mM 4-aminophenylmethanesulfonyl fluoride. The resulting cells were disrupted by ultrasonication using Branson Sonifier (manufactured by Branson Ultrasonics). Then, the resulting cell lysate was centrifuged at 20,000×g for 60 minutes, to remove cell debris, and the resulting supernatant was dialyzed against 20 mM potassium phosphate buffer (pH 8.5) containing 0.05 mM PLP. The solution after dialysis was heated at 65° C. for 30 minutes, to remove heat-denatured *Escherichia coli* protein including tryptophan indole-lyase derived from *Escherichia coli*. Thereafter, the resulting products were cooled on ice. The protein aggregate was removed by centrifugation at 5,000×g for 20 minutes, and the resulting supernatant was used as an enzyme solution. The above-mentioned enzyme solution was stored at −20° C. until use.

4) Determination of L-Tryptophan Synthesizing Activity

L-Tryptophan synthesizing activity of TNA was determined in the mixture (pH 8.5) containing 25 mM indole, 100 mM sodium pyruvate and 500 mM ammonium chloride. The reaction was initiated by addition of the enzyme solution and stopped after the incubation for 20 minutes at 65° C. by addition of 0.05 ml of 5 N HCl. L-Tryptophan generated was measured by HPLC equipped with a reverse-phase column (manufactured by Waters, trade name: µBondapak C18). Elution was performed at a flow rate of 1 ml/minute using a solution containing 5% (v/v) methanol, 2%(v/v) acetic acid and 0.1 M sodium phosphate buffer (pH 6.5). Detection of protein was performed by an absorptiometer at 280 nm. One unit of the enzyme was defined as the amount of the enzyme catalyzing the synthesis of 1 µmol L-tryptophan per minute under the above-mentioned conditions. The specific activity was represented by units for one milligram of the enzyme. The protein concentration was determined by the Bradford method using bovine serum albumin (manufactured by Sigma) as the standard.

5) Production of L-Tryptophan

Production of L-tryptophan was carried out using an agitating reactor. In order to inhibit oxidization of substrate indole, the enzyme reactor was filled with nitrogen gas. The reaction temperature was controlled at 37° C. by water circulation through a water-jacket. In order to prevent depletion of the substrate, the concentration of indole was determined by HPLC and thereafter, indole and sodium pyruvate were intermittently supplied to the reaction solution.

6) Growth Curve of Cells

The optical density (OD) of a cell culture was determined at 600 nm using a absorptiometer (trade name: BioChrom 4060, manufactured by Pharmacia).

7) Large-Scale Production of TNA

Figure 9:
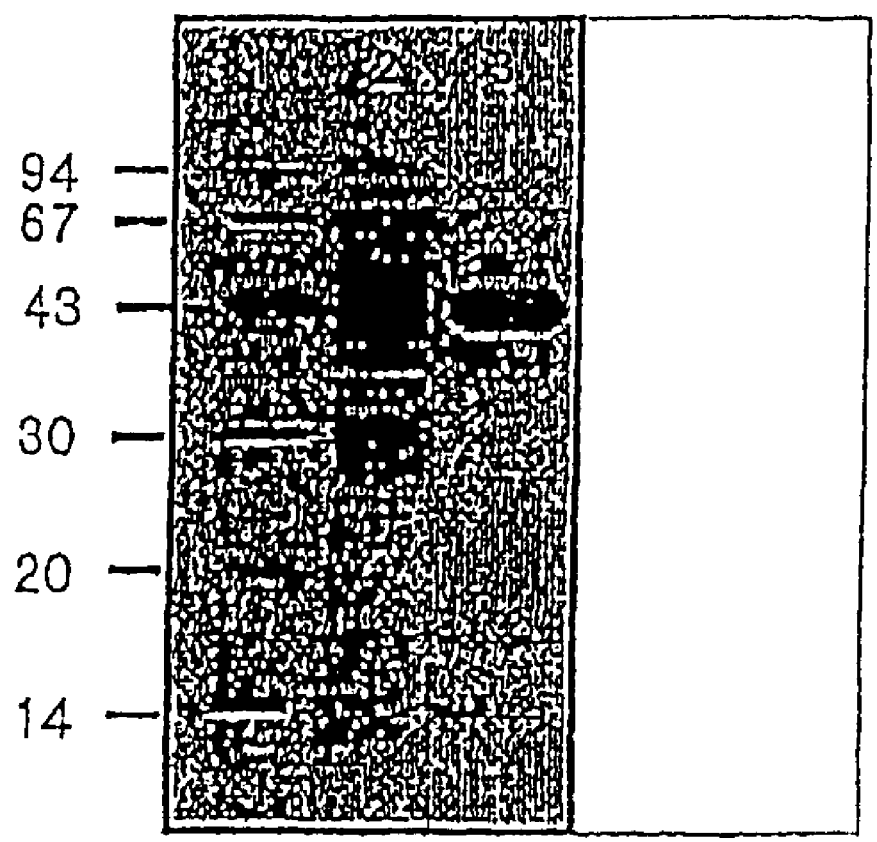
FIG. 9 is a view showing the results of SDS-PAGE analysis of expression of TNA in *Escherichia coli* harboring the expression vector pHCE19T(II)-TNA.

According to the above-mentioned items 1)-6), the production of TNA was carried out by using *Escherichia coli* (HB101/pHCE19T(II)-TNA) harboring pHCE19T(II)-TNA. As a result, as shown in FIG. 9, the protein was expressed in the content of approximately 40% of the total cellular proteins of *Escherichia coli*. In order to achieve large-scale production of TNA under the conditions in high cell growth in the batch culture, *Escherichia coli* HB101/pHCE19T(II)-TNA was cultured in complex medium containing 50 g/l glycerol.

Figure 10:
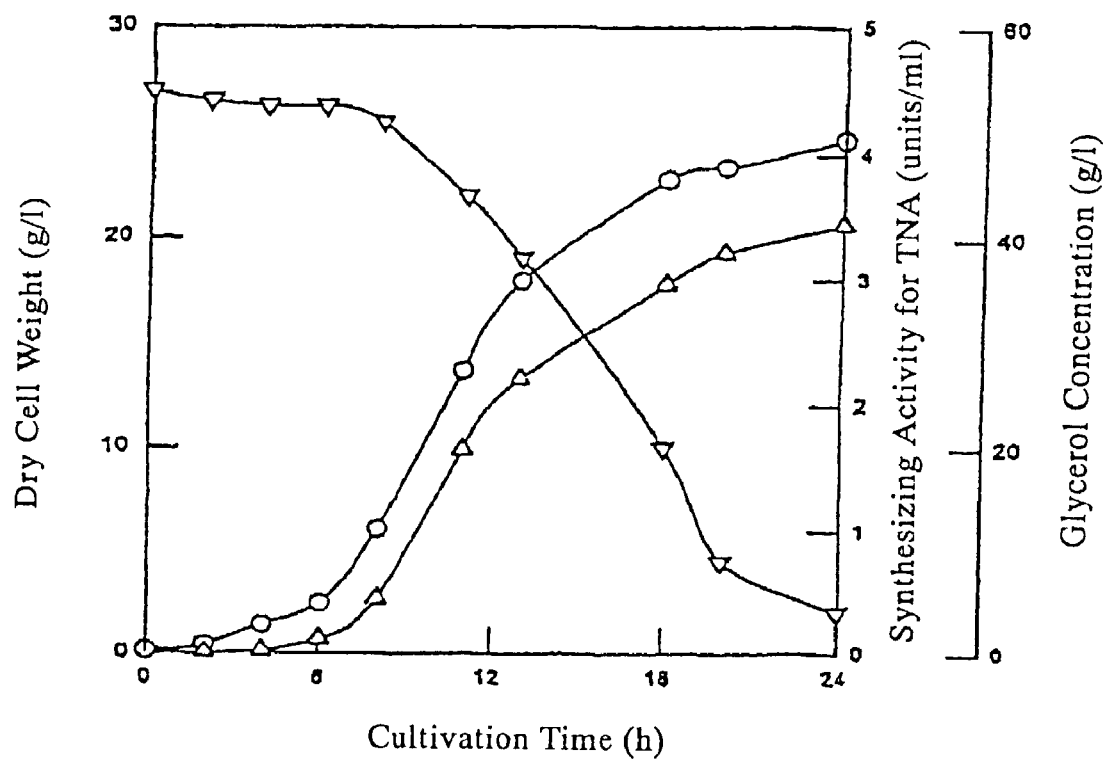
FIG. 10 is a graph showing the analytical results of growth curve of *Escherichia coli* HB101/pHCE19T(II)-TNA, the synthesizing activity for TNA and the expression product, and showing a typical profile for batch culture of *Escherichia coli* HB101/pHCE19T(II)-TNA at 37° C. in a 2.5 L fermenter.

Profile for the batch culture of *Escherichia coli* HB101/pHCE19T(II)-TNA at 37° C. in a 2.5 L fermentor is shown in FIG. 10. In the figure, the open circles indicate dry weights of the cells (g/L), open upright triangles indicate TNA synthesis activity (units/ml), and open inverted triangles indicate glycerol concentrations (g/L). After three-hour culturing, TNA production was increased along with cell growth. When cultured for 20 hours, the cell growth rate and the rate of TNA production reached to the maximum levels. The final cell concentration reached to 75 in absorbance at 600 nm in 24 hours, and the maximum TNA activity reached to 3.450 units/ml. The TNA production level increased 9.2-folds that of the production level obtained when the cells harboring plasmids with lac-promoters were cultured in LB medium under inducing conditions for IPTG.

After SDS-PAGE, the protein band was analyzed using a scanning densitometer. As a result, the content of the soluble enzyme was deduced as approximately 40% of the total cellular proteins in the extract of *Escherichia coli*. Most of the TNA expressed in the cells were produced in the soluble form.

The specific activity for L-tryptophan synthesis in the crude extract of *Escherichia coli* HB101/pHCE19T(II)-TNA was approximately 0.15 units/mg cells. This result suggests that the thermostable enzyme including thermostable tryptophan indole-lyase can be expressed efficiently by the constitutive promoter.

EXAMPLE 6

Effects of Various Reaction Conditions on Production of L-Tryptophan

1) Temperature

In order to study the thermal stability of TNA, TNA was incubated at various temperatures for 30 minutes in 50 mM potassium phosphate buffer (pH 8.5), and thereafter remaining activities were determined. An enzyme solution obtained after heat treatment of a cell-free extract at 60° C. was used as a biocatalyst of this experiment.

Figure 11:
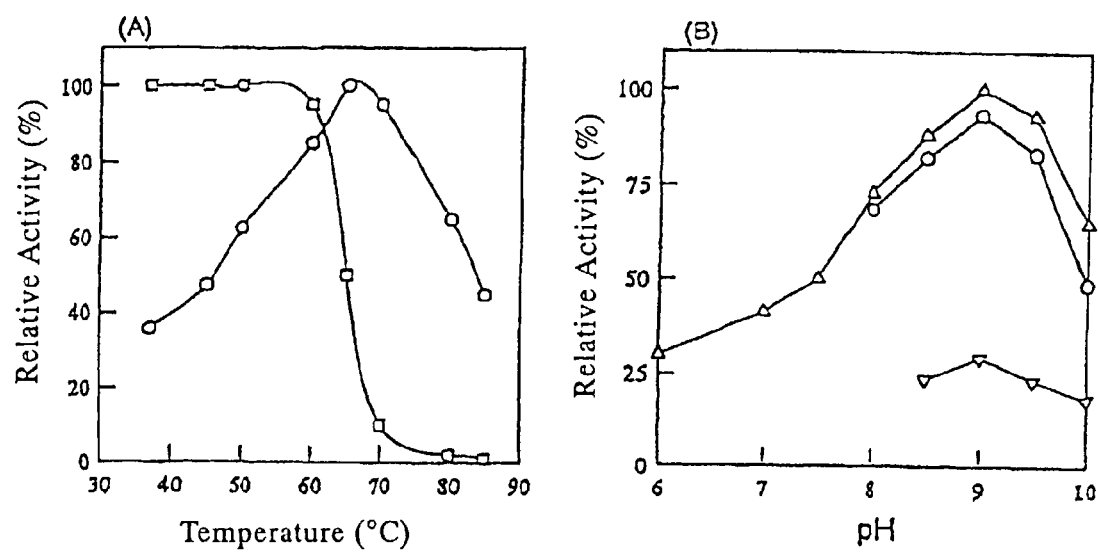
FIG. 11 is a graph each showing effects of temperature and pH on the synthesizing activity for TNA.

As shown in FIG. 11, this enzyme was stable up to 60° C., and 95% of the enzyme activity thereof was maintained after the heat treatment. Since the stability of TNA is thought to be a main factor for determining the productivity in the synthesis of L-tryptophan, TNA is considered to have excellent possibilities in improving the enzymatic method. In addition, the maximum reaction temperature for synthesizing L-tryptophan was 65° C.

2) pH

The effect of pH on the rate of the L-tryptophan synthesis by TNA was studied in the presence of excess ammonium chloride and sodium pyruvate. The reaction was carried out in each of buffers having various pH's. As shown in FIG. 11, the effect of pH on the synthesis activity of TNA is considerably significant, and the maximum activity of TNA for L-tryptophan synthesis was found at pH 9.0. In glycine/NaOH buffer, there was observed drastic inhibition to the enzyme reaction.

3) Ammonium Donor

In order to select the most suitable ammonium donor in the synthesis of L-tryptophan, for a reaction mixture, there were used various ammonium salts such as ammonium acetate, ammonium chloride, ammonium citrate, ammonium formate, ammonium nitrate, ammonium oxalate, diammonium hydrogenphosphate, and ammonium sulfate. The results are shown in Table 1.

TABLE 1

| Ammonium Donor | Relative Activity (%) |
| --- | --- |
| Ammonium acetate | 85.8 |
| Ammonium chloride | 100 |
| Ammonium formate | 58.8 |
| Diammonium hydrogenphosphate | 82.4 |
| Ammonium nitrate | 62.3 |
| Diammonium sulfate | 80.4 |

Reaction Conditions:
5 mM or 25 mM indole, 200 mM sodium pyruvate, 1.0M ammonium donor, pH9.0, 60° C.

As shown in Table 1, ammonium chloride was the most suitable ammonium donor in the synthesis of L-tryptophan. The tryptophan synthesizing activity of TNA in the case where ammonium acetate or diammonium hydrogenphosphate was used was about 80% of the activity when ammonium chloride was used. In addition, the effect of ammonium chloride in the concentration range of 0–1.5 M on the synthesis of L-tryptophan was shown in FIG. 12 panel (A). The synthesizing activity was largely dependent on the concentration of ammonium chloride and had almost the same level as that of 1.0–1.5 M ammonium chloride.

4) Indole Concentration

Figure 12:
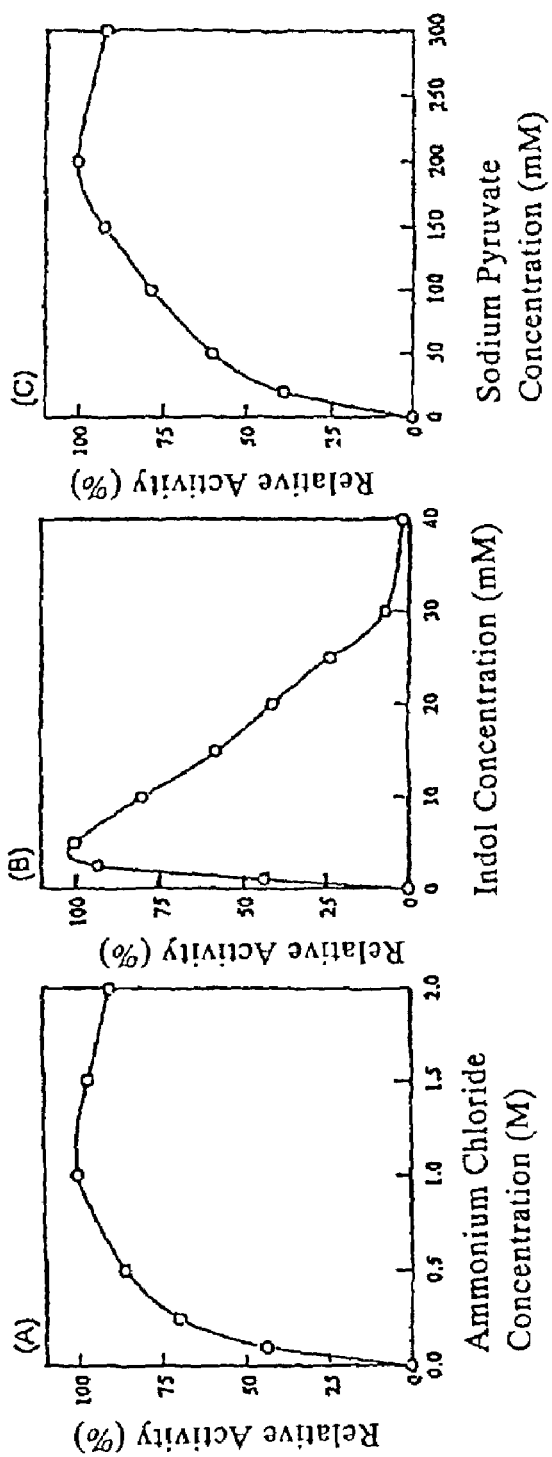
FIG. 12 is a graph each showing effects of ammonium chloride concentration, indol concentration and sodium pyruvate concentration on the synthesizing activity for TNA.

Since thermostable enzymes tend to be stable toward chemical-modifying agents, there can be provided remarkable advantages in biotechnological processes using enzymes as a biocatalyst. In order to evaluate the stability of the TNA, the effect of the indole concentration on the productivity of thermostable TNA was investigated. As shown in FIG. 12 panel (B), although the tryptophan synthesizing activity of TNA was increased to an indole concentration of 5 mM, the activity was decreased in stages after exceeding the concentration because of the toxicity of indole. Concurrently, TNA of *Escherichia coli* was completely inactivated at 3 mM of indole. This result indicates that those of *Symbiobacterium toebii* has a relatively high stability for inactivation of enzyme by indole, as compared with those of *Escherichia coli*.

5) Concentration of Sodium Pyruvate

FIG. 12 panel (C) shows the results of studying the L-tryptophan synthesizing activities by TNA at a variety of concentrations within the range of from 0 to 300 mM of sodium pyruvate. The rate of tryptophan production was linearly increased in proportion to the concentration of sodium pyruvate. The maximum synthesizing activity was obtained at a pyruvate concentration of 0.1 M. After exceeding the concentration, the rate of tryptophan synthesis was kept at a similar value.

6) Triton™ X-100

Figure 13:
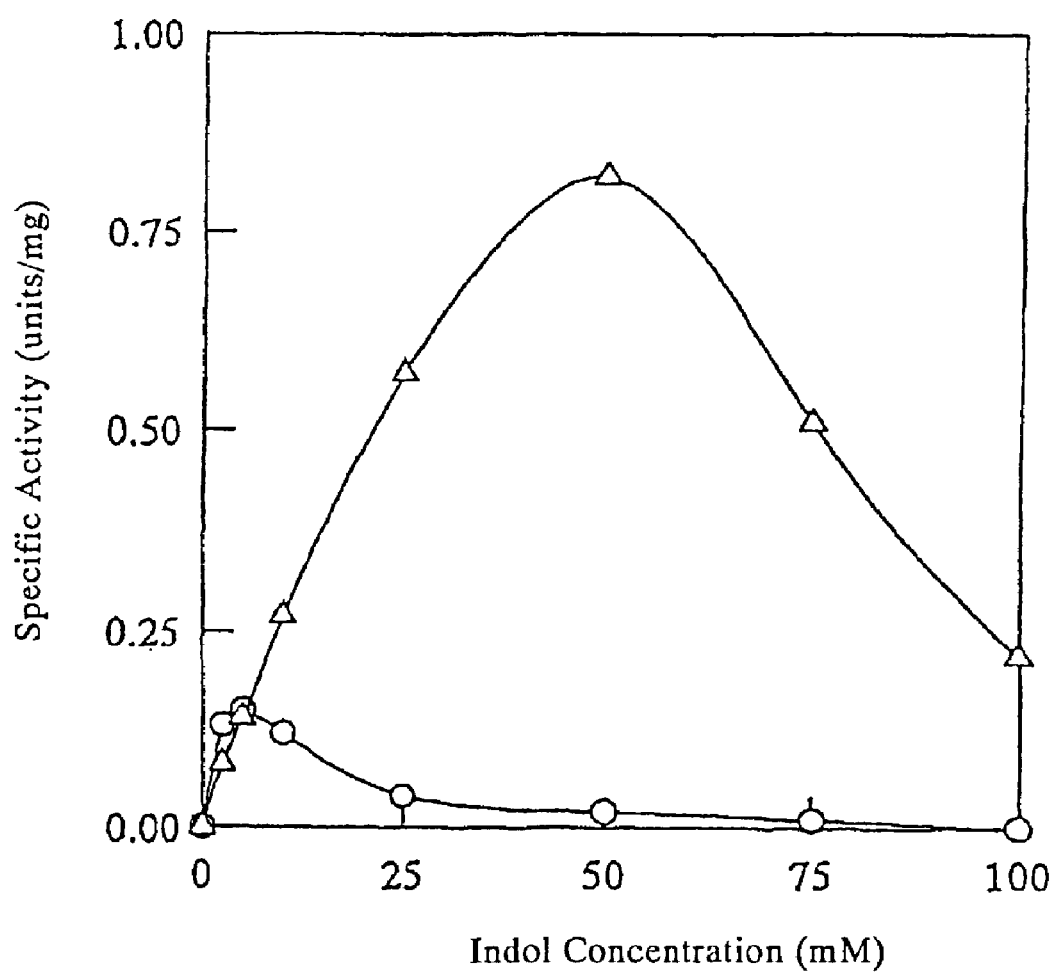
FIG. 13 is a graph showing effects of Triton X-100 on the synthesizing activity for TNA.

Nonionic surfactants such as Triton X-100 form micelles to include indole therein and thus function as reservoirs for indole during the enzyme reaction for the synthesis of L-tryptophan. Therefore, the effects of Triton X-100 on the rate of L-tryptophan production were studied and the production rate was compared with the production rate in a reaction mixture without Triton X-100. The results are shown in FIG. 13. In a reaction mixture with 3% (v/v) Triton X-100, the maximum rate of L-tryptophan synthesis was obtained at an indole concentration of 50 mM which was 10 times higher than that of a reaction mixture without Triton X-100. After exceeding the concentration, the productivity of L-tryptophan was reduced.

7) Optimization of Pre-Treatment of Biocatalysts for Production of L-Tryptophan

In order to compare the efficiencies of various biocatalysts on the production of L-tryptophan, a biocatalyst containing a cell-free extract, intact whole cells, penetrated cells and acetone-dried cells were added to a reaction mixture containing 5 mM or 25 mM indole. The penetrated cells were prepared by treating the whole cells with toluene or methanol and then centrifuging. The acetone-dried cells were obtained by treating the whole cells with acetone and subsequently drying the cells with air-stream. The concentrations of sodium pyruvate and ammonium chloride were 200 mM and 1 M, respectively.

TABLE 2

| Type of Biocatalysts | Relative Activity (%) (5 mM indole) | Relative Activity (%) (25 mM indole) |
|---|---|---|
| Whole intact cells | 100 | 100 |
| Cell-free extract | 98.2 | 75.5 |
| Cell treated with 5% methanol | 98.5 | 78.9 |
| Cell treated with 10% methanol | 97.5 | 71.7 |
| Cell treated with 5% toluene | 95.5 | 69.9 |
| Cell treated with 10% toluene | 90.2 | 53.3 |
| Cell dried with acetone | 97.5 | 62.4 |

Reaction conditions:
5 mM or 25 mM indole, 200 mM sodium pynivate, 1.0M ammonium chloride, pH9.0, 37° C.

As shown in Table 2, L-tryptophan was effectively synthesized in all the biocatalysts tested at a low concentration of indole (5 mM). Concurrently, only the intact cells showed a high L-tryptophan synthesizing activity at a high concentration of indole (25 mM). In this case, other biocatalysts of a lower activity seem to be caused by the inhibition of enzyme through the direct interaction between the enzyme and high concentration of localized indole. The results show that the whole cells are the most suitable biocatalyst for an efficient production of L-tryptophan. Therefore, the whole cells in which TNA was excessively produced were used as a biocatalyst for the production of L-tryptophan.

8) Production of L-Tryptophan by Whole Cell Biocatalyst

Pyruvate as a substrate is very unstable at a temperature higher than 45° C., and at this temperature, pyruvate immediately disappears in a reaction mixture as deduced by reduction via NADH in the presence of lactate dehydrogenase. The formation of imines with ammonia was probably the main reaction responsible to a decrease in pyruvate. However, it could not remove the occurrence of a further reaction of pyruvate. Because of the thermal instability of pyruvate, the synthesis reaction cannot stably proceed at 65° C. Therefore, large-scale quantity of L-tryptophan could not be produced. Accordingly, the production of L-tryptophan was performed at 37° C. in 1 liter of the reaction mixture in an enzyme reactor.

The starting reaction mixture comprises 1.0 M ammonium chloride, 100 mM sodium pyruvate, 30 mM indole, 0.1 mM PLP, 0.1% sodium sulfite and 10 g (dried weight)/l of *Escherichia coli* HB101/pHCE19T(II)-TNA cells. 3% Triton X-100 was added to the reaction mixture, and the added indole was solubilized. In order to prevent depletion of the substrate, indole and sodium pyruvate were continuously supplied to the reaction solution.

Figure 14:
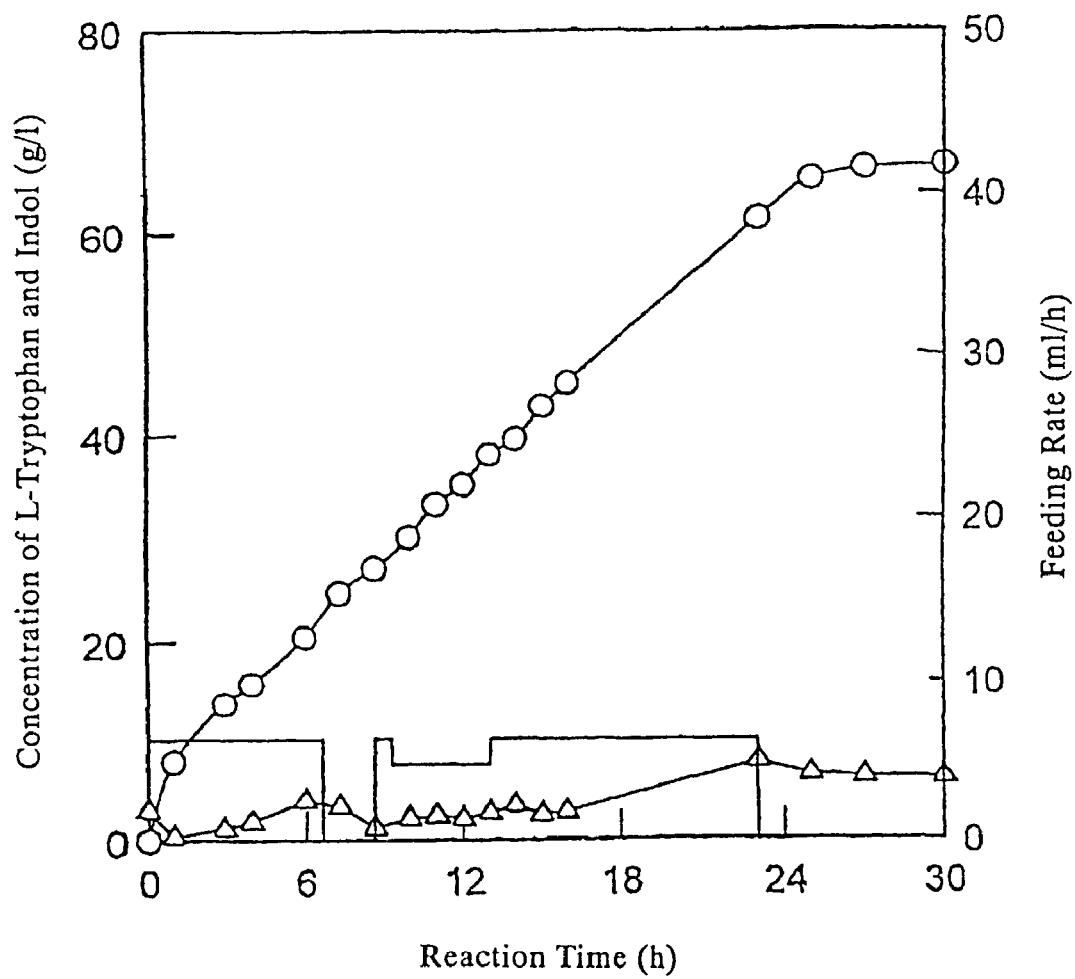
FIG. 14 is a view showing a reaction pattern of L-tryptophan production in an enzyme reactor.

FIG. 14 shows a reaction pattern of the production of L-tryptophan in the enzyme reactor. The rate of L-tryptophan production was maintained at the same level for 27 hours, and then gradually decreased. By the analysis of the reaction mixture by means of HPLC, this reduction of the rate of L-tryptophan production was found to be caused by the inhibition due to the indole accumulated in a large amount in the reactor. From three hours after starting the reaction, L-tryptophan began to precipitate as a white crystal, whereby the reaction was allowed to efficiently proceed. Twenty-four hours after starting the reaction, approximately 66.2 g/l (0.325 M) of L-tryptophan was produced at 37° C. from the indole at a conversion efficiency of 85%.

SEQUENCE LISTING FREE TEXT

SEQ ID NO: 1 shows a sequence of a promoter region in pHCE19T(II).

SEQ ID NO: 2 shows a sequence of a promoter region in pHCE19(II).

SEQ ID NO: 3 shows a sequence of pHCE19T(II).

SEQ ID NO: 4 shows a sequence of pHCE19(II).

SEQ ID NO: 5 shows a sequence of an oligonucleotide sequence for amplifying a promoter of D-AAT gene derived from *Bacillus* sp.

SEQ ID NO: 6 shows a sequence of an oligonucleotide sequence for amplifying a promoter of D-AAT gene derived from *Bacillus* sp.

SEQ ID NO: 7 shows a sequence of an oligonucleotide sequence for amplifying a promoter of D-AAT gene derived from *Bacillus* sp.

SEQ ID NO: 8 shows a sequence of an oligonucleotide sequence for amplifying TNA gene derived from *Symbiobacterium toebii* SC-1.

SEQ ID NO: 9 shows a sequence of an oligonucleotide sequence for amplifying TNA gene derived from *Symbiobacterium toebii* SC-1.

INDUSTRIAL APPLICABILITY

According to the DNA of the present invention, since the DNA has a promoter sequence capable of constitutively expressing a desired gene product, without inducing by an inducer, there are exhibited excellent effects that the desired gene product can be expressed easily and inexpensively at a high level. Therefore, the DNA of the present invention allows to produce an expression product for a useful gene in industrial scale. In addition, the method for producing a protein of the present invention allows to produce an expression product for a useful gene in industrial scale.

The invention claimed is:

1. An isolated DNA, wherein the isolated DNA exhibits a constitutive promoter activity in *Escherichia coli* or a bacterium belonging to the genus *Bacillus*, and wherein the isolated DNA has a nucleotide sequence selected from the group consisting of:
   (A) the nucleotide sequence of SEQ ID NO: 1; and
   (B) a nucleotide sequence having at least 80% sequence identity to the nucleotide sequence of SEQ ID NO: 1.

2. The isolated DNA according to claim 1, wherein the isolated DNA is capable of expressing a foreign gene in the absence of an inducer, when located upstream from the gene.

3. A recombinant DNA comprising the DNA of claim 1 and a foreign gene, wherein the foreign gene is operably located.

4. The recombinant DNA according to claim 3, wherein the foreign gene is a nucleic acid selected from the group consisting of a nucleic acid encoding a protein, a nucleic acid encoding antisense RNA, and a nucleic acid encoding a ribozyme.

5. A gene expression vector, at least comprising the DNA of claim 1.

6. The gene expression vector according to claim 5, wherein the vector is a vector selected from the group consisting of plasmid vectors, phage vectors and viral vectors.

7. The gene expression vector according to claim 5 or 6, which comprises the nucleotide sequence of SEQ ID NO: 3.

8. An expression vector comprising the recombinant DNA of claim 3.

9. The expression vector according to claim 8, wherein the vector is a vector selected from the group consisting of plasmid vectors, phage vectors and viral vectors.

10. A transformant of *Escherichia coli* or a *Bacillus* bacterium having the recombinant DNA of claim 3 or 4.

11. A method for producing a protein, comprising:
    culturing the transformant of claim 10, and
    collecting a protein from the resulting culture.

12. A kit for producing a protein, at least comprising DNA of claim 1 or 2, or a gene expression vector at least comprising the DNA of claim 1 or 2.

13. A transformant of *Escherichia coli* or a *Bacillus* bacterium having the expression vector of claim 8 or 9.

* * * * *

SEQUENCE LISTING

<160> NUMBER OF SEQ ID NOS: 10
<210> SEQ ID NO 1
<211> LENGTH: 223
<212> TYPE: DNA
<213> ORGANISM: Artificial Sequence
<220> FEATURE:
<223> OTHER INFORMATION: A sequence for promoter region on pHCE19T(II).

<400> SEQUENCE: 1

```
gatctctcct tcacagattc ccaatctctt gttaaataac gaaaaagcat caatcaaaac     60
ggcggcatgt ctttctatat tccagcaatg ttttataggg gacatattga tgaagatggg    120
tatcaccttat gtaaaaaaag aattgctata agctgctctt ttttgttcgt gatatactga   180
taataaattg aattttcaca cttctggaaa aggagatat acc                       223
```

<210> SEQ ID NO 2
<211> LENGTH: 225
<212> TYPE: DNA
<213> ORGANISM: Artificial Sequence
<220> FEATURE:
<223> OTHER INFORMATION: A sequence for promoter region on pHCE19(II).

<400> SEQUENCE: 2

```
gatctctcct tcacagattc ccaatctctt gttaaataac gaaaaagcat caatcaaaac     60
ggcggcatgt ctttctatat tccagcagtg ttttataggg gacatattga tgaagatggg    120
tatcaccttat gtaaaaaaag aattgctata agctgctctt ttttgttcgt gatatactga   180
taataaattg aattttcaca cttctggaaa aggagctgg aaccc                     225
```

<210> SEQ ID NO 3
<211> LENGTH: 3753
<212> TYPE: DNA
<213> ORGANISM: Artificial Sequence
<220> FEATURE:
<223> OTHER INFORMATION: A sequence for pHCE19T(II).

<400> SEQUENCE: 3

```
gatctctcct tcacagattc ccaatctctt gttaaataac gaaaaagcat caatcaaaac     60
ggcggcatgt ctttctatat tccagcaatg ttttataggg gacatattga tgaagatggg    120
tatcaccttat gtaaaaaaag aattgctata agctgctctt ttttgttcgt gatatactga   180
taataaattg aattttcaca cttctggaaa aggagatat accatggaat tcgagctcgg    240
tacccgggga tcctctagag tcgacctgca ggcatgcaag cttggctgtt ttggcggatg    300
agagaagatt ttcagcctga tacagattaa atcagaacgc agaagcggtc tgataaaaca    360
gaatttgcct ggcggcagta gcgcggtggt cccacctgac cccatgccga actcagaagt    420
gaaacgccgt agcgccgatg gtagtgtggg gtctccccat gcgagagtag ggaactgcca    480
ggcatcaaat aaaacgaaag gctcagtcga agactgggc ctttcgtttt atctgttgtt    540
tgtcggtgaa cgctctcctg agtaggacaa atccgccggg agcggatttg aacgttgcga    600
agcaacggcc cggagggtgg cgggcaggac gcccgccata aactgccagg catcaaatta    660
agcagaaggc catcctgacg gatggccttt ttgcgtttct acaaactctt tttgtttatt    720
tttctaaata cattcaaata tgtatccgct catgagacaa taaccctgat aaatgcttca    780
ataatattga aaaggaaga gtatgagtat tcaacatttc cgtgtcgccc ttattccctt    840
ttttgcggca ttttgccttc ctgttttttgc tcacccagaa acgctggtga agtaaaaga    900
```

-continued

```
tgctgaagat cagttgggtg cacgagtggg ttacatcgaa ctggatctca acagcgtaa     960
gatccttgag agttttcgcc ccgaagaacg ttttccaatg atgagcactt ttaaagttct   1020
gctatgtggc gcggtattat cccgtgttga cgccgggcaa gagcaactcg gtcgccgcat   1080
acactattct cagaatgact tggttgagta attcactggc cgtcgtttta caacgtcgtg   1140
actgggaaaa ccctggcgtt acccaactta atcgccttgc agcacatccc cctttcgcca   1200
gctggcgtaa tagcgaagag gcccgcaccg atcgcccttc ccaacagttg cgcagcctga   1260
atggcgaatg gcgcctgatg cggtattttc tccttacgca tctgtgcggt atttcacacc   1320
gcatatggtg cactctcagt acaatctgct ctgatgccgc atagttaagc cagccccgac   1380
acccgccaac acccgctgac gcgccctgac gggcttgtct gctcccggca tccgcttaca   1440
gacaagctgt gaccgtctcc gggagctgca tgtgtcagag gttttcaccg tcatcaccga   1500
aacgcgcgag acgaaagggc ctcgtgatac gcctattttt ataggttaat gtcatgataa   1560
taatggtttc ttagacgtca ggtggcactt ttcggggaaa tgtgcgcgga cccctatttt   1620
gtttattttt ctaaatacat tcaaatatgt atccgctcat gagacaataa ccctgataaa   1680
tgcttcaata atattgaaaa aggaagagta tgagtattca actttccgt gtcgccctta   1740
ttccctttt tgcggcattt tgccttcctg tttttgctca cccagaaacg ctggtgaaag   1800
taaaagatgc tgaagatcag ttgggtgcac gagtgggtta catcgaactg gatctcaaca   1860
gcggtaagat ccttgagagt tttcgccccg aagaacgttt tccaatgatg agcactttta   1920
aagttctgct atgtggcgcg gtattatccc gtattgacgc cgggcaagag caactcggtc   1980
gccgcataca ctattctcag aatgacttgg ttgagtactc accagtcaca gaaaagcatc   2040
ttacggatgg catgacagta agagaattat gcagtgctgc cataaccatg agtgataaca   2100
ctgcggccaa cttacttctg acaacgatcg gaggaccgaa ggagctaacc gcttttttgc   2160
acaacatggg ggatcatgta actcgccttg atcgttggga accggagctg aatgaagcca   2220
taccaaacga cgagcgtgac accacgatgc ctgtagcaat ggcaacaacg ttgcgcaaac   2280
tattaactgg cgaactactt actctagctt cccggcaaca attaatagac tggatggagg   2340
cggataaagt tgcaggacca cttctgcgct cggcccttcc ggctggctgg tttattgctg   2400
ataaatctgg agccggtgag cgtgggtctc gcggtatcat tgcagcactg ggccagatg    2460
gtaagccctc ccgtatcgta gttatctaca cgacggggag tcaggcaact atggatgaac   2520
gaaatagaca gatcgctgag ataggtgcct cactgattaa gcattggtaa ctgtcagacc   2580
aagtttactc atatatactt tagattgatt taaaacttca ttttttaattt aaaaggatct   2640
aggtgaagat cctttttgat aatctcatga ccaaaatccc ttaacgtgag ttttcgttcc   2700
actgagcgtc agaccccgta gaaaagatca aaggatcttc ttgagatcct ttttttctgc   2760
gcgtaatctg ctgcttgcaa acaaaaaaac caccgctacc agcggtggtt tgtttgccgg   2820
atcaagagct accaactctt tttccgaagg taactggctt cagcagagcg cagataccaa   2880
atactgtcct tctagtgtag ccgtagttag gccaccactt caagaactct gtagcaccgc   2940
ctacatacct cgctctgcta atcctgttac cagtggctgc tgccagtggc gataagtcgt   3000
gtcttaccgg gttggactca agacgatagt taccggataa ggcgcagcgg tcgggctgaa   3060
cggggggttc gtgcacacag cccagcttgg agcgaacgac ctacaccgaa ctgagatacc   3120
tacagcgtga gcattgagaa agcgccacgc ttcccgaagg gagaaaggcg gacaggtatc   3180
cggtaagcgg cagggtcgga acaggagagc gcacagggga gcttccaggg ggaaacgcct   3240
ggtatcttta tagtcctgtc gggtttcgcc acctctgact gagcgtcga ttttttgtgat   3300
```

-continued

```
gctcgtcagg ggggcggagc ctatggaaaa acgccagcaa cgcggccttt ttacggttcc      3360
tggccttttg ctggccttt tgctcacatgt tctttcctgc gttatcccct gattctgtgg      3420
ataaccgtat taccgccttt gagtgagctg ataccgctcg ccgcagccga acgaccgagc      3480
gcagcgagtc agtgagcgag gaagcggaag agcgcccaat acgcaaaccg cctctccccg      3540
cgcgttggcc gattcattaa tgcagctggc acgacaggtt cccgactgga aagcgggca      3600 gtgagcgcaa cgcaattaat gtgagttagc tcactcatta ggcaccccag ctttacact      3660 ttatgcttcc ggctcgtatg ttgtgtggaa ttgtgagcgg ataacaattt cacacaggaa      3720
acagctatga ccatgattac gccaagctag ctt                                   3753
```

<210> SEQ ID NO 4
<211> LENGTH: 3755
<212> TYPE: DNA
<213> ORGANISM: Artificial Sequence
<220> FEATURE:
<223> OTHER INFORMATION: A sequence for pHCE19(II).

<400> SEQUENCE: 4

```
gatctctcct tcacagattc ccaatctctt gttaaataac gaaaaagcat caatcaaaac        60
ggcggcatgt cttctatat tccagcagtg ttttataggg gacatattga tgaagatggg       120 tatcaccttα gtaaaaaaag aattgctata agctgctctt ttttgttcgt gatatactga      180
taataaattg aattttcaca cttctggaaa aaggagctgg aacccatgga attcgagctc      240
ggtacccggg gatcctctag agtcgacctg caggcatgca agcttggctg ttttggcgga      300
tgagagaaga ttttcagcct gatacagatt aaatcagaac gcagaagcgg tctgataaaa      360
cagaatttgc ctggcggcag tagcgcggtg gtcccacctg accccatgcc gaactcagaa      420
gtgaaacgcc gtagcgccga tggtagtgtg gggtctcccc atgcgagagt agggaactgc      480
caggcatcaa ataaaacgaa aggctcagtc gaaagactgg gcctttcgtt ttatctgttg      540
tttgtcggtg aacgctctcc tgagtaggac aaatccgccg ggagcggatt tgaacgttgc      600
gaagcaacgg cccggagggt ggcgggcagg acgcccgcca taaactgcca ggcatcaaat      660
taagcagaag gccatcctga cggatggcct ttttgcgttt ctacaaactc ttttttgttta      720 tttttctaaa tacattcaaa tatgtatccg ctcatgagac aataaccctg ataaatgctt      780
caataatatt gaaaaaggaa gagtatgagt attcaacatt tccgtgtcgc ccttattccc      840
ttttttgcgg cattttgcct tcctgttttt gctcacccag aaacgctggt gaaagtaaaa      900
gatgctgaag atcagttggg tgcacgagtg ggttacatcg aactggatct caacagcggt      960
aagatccttg agagttttcg ccccgaagaa cgttttccaa tgatgagcac ttttaaagtt     1020
ctgctatgtg gcgcggtatt atcccgtgtt gacgccgggc aagagcaact cggtcgccgc     1080
atacactatt ctcagaatga cttggttgag taattcactg gccgtcgttt tacaacgtcg     1140
tgactgggaa aaccctggcg ttacccaact taatcgcctt gcagcacatc cccctttcgc     1200
cagctggcgt aatagcgaag aggcccgcac cgatcgccct tcccaacagt tgcgcagcct     1260
gaatggcgaa tggcgcctga tgcggtattt tctccttacg catctgtgcg gtatttcaca     1320
ccgcatatgg tgcactctca gtacaatctg ctctgatgcc gcatagttaa gccagccccg     1380
acacccgcca acacccgctg acgcgccctg acgggcttgt ctgctcccgg catccgctta     1440
cagacaagct gtgaccgtct ccgggagctg catgtgtcag aggttttcac cgtcatcacc     1500
gaaacgcgcg agacgaaagg gcctcgtgat acgcctattt ttataggtta atgtcatgat     1560
```

```
aataatggtt tcttagacgt caggtggcac ttttcgggga aatgtgcgcg gaacccctat    1620
ttgtttattt ttctaaatac attcaaatat gtatccgctc atgagacaat aaccctgata    1680
aatgcttcaa taatattgaa aaaggaagag tatgagtatt caacatttcc gtgtcgccct    1740
tattcccttt tttgcggcat tttgccttcc tgttttttgct cacccagaaa cgctggtgaa    1800
agtaaaagat gctgaagatc agttgggtgc acgagtgggt tacatcgaac tggatctcaa    1860
cagcggtaag atccttgaga gttttcgccc cgaagaacgt tttccaatga tgagcacttt    1920
taaagttctg ctatgtggcg cggtattatc ccgtattgac gccgggcaag agcaactcgg    1980
tcgccgcata cactattctc agaatgactt ggttgagtac tcaccagtca cagaaaagca    2040
tcttacggat ggcatgacag taagagaatt atgcagtgct gccataacca tgagtgataa    2100
cactgcggcc aacttacttc tgacaacgat cggaggaccg aaggagctaa ccgcttttt    2160 gcacaacatg ggggatcatg taactcgcct tgatcgttgg gaaccggagc tgaatgaagc    2220
cataccaaac gacgagcgtg acaccacgat gcctgtagca atggcaacaa cgttgcgcaa    2280
actattaact ggcgaactac ttactctagc ttcccggcaa caattaatag actggatgga    2340
ggcggataaa gttgcaggac cacttctgcg ctcggccctt ccggctggct ggtttattgc    2400
tgataaatct ggagccggtg agcgtgggtc tcgcggtatc attgcagcac tggggccaga    2460
tggtaagccc tcccgtatcg tagttatcta cacgacgggg agtcaggcaa ctatggatga    2520
acgaaataga cagatcgctg agataggtgc ctcactgatt aagcattggt aactgtcaga    2580
ccaagtttac tcatatatac tttagattga tttaaaactt catttttaat ttaaaaggat    2640
ctaggtgaag atcctttttg ataatctcat gaccaaaatc ccttaacgtg agttttcgtt    2700
ccactgagcg tcagaccccg tagaaaagat caaaggatct tcttgagatc ctttttttct    2760
gcgcgtaatc tgctgcttgc aaacaaaaaa accaccgcta ccagcggtgg tttgtttgcc    2820
ggatcaagag ctaccaactc ttttccgaa ggtaactggc ttcagcagag cgcagatacc    2880
aaatactgtc cttctagtgt agccgtagtt aggccaccac ttcaagaact ctgtagcacc    2940
gcctacatac ctcgctctgc taatcctgtt accagtggct gctgccagtg gcgataagtc    3000
gtgtcttacc gggttggact caagacgata gttaccggat aaggcgcagc ggtcgggctg    3060 aacgggggt tcgtgcacac agcccagctt ggagcgaacg acctacaccg aactgagata    3120
cctacagcgt gagcattgag aaagcgccac gcttcccgaa gggagaaagg cggacaggta    3180
tccggtaagc ggcagggtcg gaacaggaga gcgcacgagg gagcttccag ggggaaacgc    3240
ctggtatctt tatagtcctg tcgggtttcg ccacctctga cttgagcgtc gatttttgtg    3300
atgctcgtca gggggcgga gcctatggaa aaacgccagc aacgcggcct ttttacggtt    3360
cctggccttt tgctggcctt tgctcacat gttctttcct gcgttatccc ctgattctgt    3420
ggataaccgt attaccgcct ttgagtgagc tgataccgct cgccgcagcc gaacgaccga    3480
gcgcagcgag tcagtgagcg aggaagcgga agagcgccca atacgcaaac cgcctctccc    3540
cgcgcgttgg ccgattcatt aatgcagctg gcacgacagg tttcccgact ggaaagcggg    3600
cagtgagcgc aacgcaatta atgtgagtta gctcactcat taggcacccc aggctttaca    3660
ctttatgctt ccggctcgta tgttgtgtgg aattgtgagc ggataacaat ttcacacagg    3720
aaacagctat gaccatgatt acgccaagct agctt    3755
```

<210> SEQ ID NO 5
<211> LENGTH: 29
<212> TYPE: DNA
<213> ORGANISM: Artificial Sequence

```
<220> FEATURE:
<223> OTHER INFORMATION: A sequence of oligonucleotide for amplifying
      promoter sequence of D-AAT gene from Bacillus sp. SK-1. HCE
      II(N) in Figs. 4 and 6.

<400> SEQUENCE: 5
ccaagcttga tctctccttc acagattcc                                    29

<210> SEQ ID NO 6
<211> LENGTH: 44
<212> TYPE: DNA
<213> ORGANISM: Artificial Sequence
<220> FEATURE:
<223> OTHER INFORMATION: A sequence of oligonucleotide for amplifying
      promoter sequence of D-AAT gene. HCE II (C:T7) in Fig. 4.

<400> SEQUENCE: 6
gaggatccag ccatggtata tctccttttt ccagaagtgt gaaa                   44

<210> SEQ ID NO 7
<211> LENGTH: 38
<212> TYPE: DNA
<213> ORGANISM: Artificial Sequence
<220> FEATURE:
<223> OTHER INFORMATION: A sequence of oligonucleotide for amplifying
      promoter sequence of D-AAT gene from Bacillus sp. SK-1. HCE II
      (C:Original) in Fig. 6.

<400> SEQUENCE: 7
agggatccag ccatgggttc cagctccttt ttccagaa                          38

<210> SEQ ID NO 8
<211> LENGTH: 20
<212> TYPE: DNA
<213> ORGANISM: Artificial Sequence
<220> FEATURE:
<223> OTHER INFORMATION: A sequence of oligonucleotide for amplifying
      a sequence of TNA gene from Symbiobacterium toebii SC-1.

<400> SEQUENCE: 8
ccaaagggcg agccctttaa                                              20

<210> SEQ ID NO 9
<211> LENGTH: 43
<212> TYPE: DNA
<213> ORGANISM: Artificial Sequence
<220> FEATURE:
<223> OTHER INFORMATION: A sequence of oligonucleotide for amplifying
      a sequence of TNA gene from Symbiobacterium toebii SC-1.

<400> SEQUENCE: 9
tgactaagtc tgcagaagct tattagacca gatcgaagtg cgc                    43

<210> SEQ ID NO 10
<211> LENGTH: 62
<212> TYPE: DNA
<213> ORGANISM: Artificial Sequence
<220> FEATURE:
<223> OTHER INFORMATION: MCS region of pHCE19T(II) of Fig. 5 or
      pHCE19(II) of Fig. 7.

<400> SEQUENCE: 10
ccatggaatt cgagctcggt acccggggat cctctagagt cgacctgcag gcatgcaagc  60
tt                                                                 62
```